United States Patent [19]

Zondler et al.

[11] Patent Number: 4,840,662
[45] Date of Patent: Jun. 20, 1989

[54] N-(2-NITROPHENYL)-5-AMINOPYRIMIDINE DERIVATIVES AND USEFUL FOR CONTROLLING HARMFUL MICRO-ORGANISMS

[75] Inventors: Helmut Zondler, Bottmingen; Adolf Hubele, Magden; Robert Nyfeler, Basel, all of Switzerland

[73] Assignee: Ciba-Geigy Corporation, Ardsley, N.Y.

[21] Appl. No.: 631,272

[22] Filed: Jul. 16, 1984

[30] Foreign Application Priority Data

Jul. 25, 1983 [CH] Switzerland ............... 4047/83

[51] Int. Cl.$^4$ .................. A01N 25/32; C07D 239/34; C07D 407/04
[52] U.S. Cl. ........................ 71/92; 514/269; 514/274; 544/301; 544/311; 544/316; 544/317; 544/319; 544/322; 544/323
[58] Field of Search ............... 544/317, 322, 331, 301, 544/311, 316, 319, 323; 514/269, 274

[56] References Cited

U.S. PATENT DOCUMENTS 3,906,098  9/1975  Barlow et al. ............ 424/251
4,014,677  3/1977  Fischer ..................... 71/92

FOREIGN PATENT DOCUMENTS 0013143  7/1980  European Pat. Off. .
112280   6/1984  European Pat. Off. ......... 544/322
2520381  5/1975  Fed. Rep. of Germany .
6065804  6/1981  Japan ...................... 544/332
1388825  3/1975  United Kingdom .

OTHER PUBLICATIONS

Serban et al, Chem. Abst 94-65716y.
Fischer, Chem. Abst. 84-74306k.

Primary Examiner—Donald G. Daus
Assistant Examiner—C. Shen

Attorney, Agent, or Firm—Edward McC. Roberts

[57] ABSTRACT

The invention discloses novel N-(2-nitrophenyl)-5-aminopyrimidine derivatives of the general formula

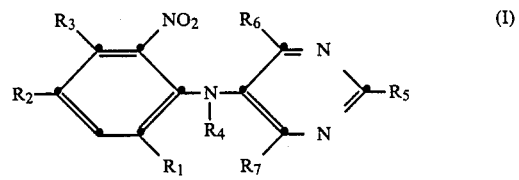

wherein
$R_1$ and $R_2$ are each independently $NO_2$ or $CF_3$, or one of $R_1$ and $R_2$ is hydrogen,
$R_3$ is hydrogen or halogen,
$R_4$ is hydrogen or the —C(O)R' group, in which R' is $C_1$–$C_4$alkyl which is unsubstituted or substituted by halogen, $C_1$–$C_3$alkoxy or $C_1$–$C_3$alkylthio,
$R_5$, $R_6$ and $R_7$ are each independently hydrogen, halogen, nitro, cyano, thiocyano, mercapto, $C_1$–$C_6$alkyl, $C_1$–$C_6$haloalkyl, $C_1$–$C_6$alkoxy, $C_1$–$C_6$alkoxy which is substituted by halogen, nitro, cyano, $C_1$–$C_3$alkoxy, $C_1$–$C_3$alkylthio and/or $N(C_1$–$C_4$alkyl)$_2$; or are $C_3$–$C_6$cycloalkoxy, $C_3$–$C_6$alkenyloxy, $C_3$–$C_6$alkynyloxy, $C_1$–$C_6$alkylthio, $C_3$–$C_6$alkenylthio, $C_1$–$C_6$alkylsulfonyl, $C_1$–$C_6$alkylsulfoxyl, $C_3$–$C_6$alkenyl, $C_3$–$C_6$haloalkenyl, $C_3$–$C_6$alkynyl, $C_3$–$C_6$haloalkynyl or the $N(C_1$–$C_4$alkyl)$_2$ group, and $R_5$ may additionally be a phenyl or benzyl group which is unsubstituted or substituted by one to three identical or different members selected from halogen, nitro, cyano, $C_1$–$C_4$alkyl, $C_1$–$C_3$haloalkyl, N—$(C_1$–$C_3$alkyl)$_2$, and/or $C_1$–$C_3$alkoxy.

The preparation of these compounds and their use in agriculture are also disclosed.

11 Claims, No Drawings

N-(2-NITROPHENYL)-5-AMINOPYRIMIDINE DERIVATIVES AND USEFUL FOR CONTROLLING HARMFUL MICRO-ORGANISMS

The present invention relates to the use of novel N-(2-nitrophenyl)-5-aminopyrimidine derivatives of the formula I below. The invention further relates to the preparation of these compounds and to agrochemical compositions which contain at least one of the novel compounds as active ingredient. The invention also relates to the preparation of such compositions and to the use of the novel compounds or of said compositions for controlling harmful micro-organisms, preferably phytopathogenic fungi and bacteria.

Specifically, the present invention relates to compounds of the general formula I

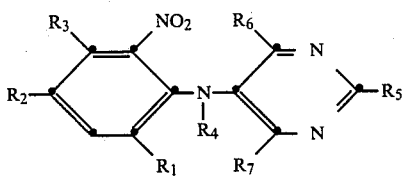

wherein
$R_1$ and $R_2$ are each independently $NO_2$ or $CF_3$, or one of $R_1$ and $R_2$ is hydrogen,
$R_3$ is hydrogen or halogen,
$R_4$ is hydrogen or the $-C(O)R'$ group, in which $R'$ is $C_1-C_4$alkyl which is unsubstituted or substituted by halogen, $C_1-C_3$alkoxy or $C_1-C_3$alkylthio,
$R_5$, $R_6$ and $R_7$ are each independently hydrogen, halogen, nitro, cyano, thiocyano, mercapto, $C_1-C_6$alkyl, $C_1-C_6$haloalkyl, $C_1-C_6$-alkoxy, $C_1-C_6$alkoxy which is substituted by halogen, nitro, cyano, $C_1-C_3$alkoxy, $C_1-C_3$alkylthio and/or $N(C_1-C_4$alkyl$)_2$; or are $C_3-C_6$cycloalkoxy, $C_3-C_6$alkenyloxy, $C_3-C_6$alkynyloxy, $C_1-C_6$-alkylthio, $C_3-C_6$alkenylthio, $C_1-C_6$alkylsulfonyl, $C_1-C_6$alkylsulfoxyl, $C_3-C_6$alkenyl, $C_3-C_6$haloalkenyl, $C_3-C_6$alkynyl, $C_3-C_6$haloalkynyl or the $N(C_1-C_4$alkyl$)_2$ group, and $R_5$ may additionally be a phenyl or benzyl group which are both unsubstituted or substituted by one to three identical or different members selected from halogen, nitro, cyano, $C_1-C_4$alkyl, $C_1-C_3$haloalkyl, $N(C_1-C_3$alkyl$)_2$, and/or $C_1-C_3$alkoxy.

Depending on the indicated number of carbon atoms, alkyl by itself or as moiety of another substituent such as alkoxy, haloalkyl, haloalkoxy etc., denotes for example the following straight chain or branched groups: methyl, ethyl, propyl, butyl pentyl, hexyl etc. and the isomers thereof, for example isopropyl, isobutyl, tert-butyl, isopentyl etc. Throughout this specification, a substituent prefixed by "halo" indicates that said substituent may be mono- to perhalogenated. Halogen and halo signify fluorine, chlorine, bromine or iodine. Hence haloalkyl is a mono- to perhalogenated alkyl radical, for example $CHCl_2$, $CH_2F$, $CCl_3$, $CH_2Cl$, $CHF_2$, $CH_2CH_2Br$, $C_2Cl_5$, $CH_2Br$, $CHBrCl$ etc., and is preferably $CF_3$. Alkenyl is for example 1-propenyl, allyl, 1-butenyl, 2-butenyl or 3-butenyl, and chains containing several double bonds. Depending on the indicated number of carbon atoms, cycloalkyl is for example cyclopropyl, cyclobutyl, cyclopentyl, cyclohexyl, cycloheptyl, cyclooctyl etc. Alkynyl is for example 2-propynyl, propargyl, 1-butynyl, 2-butynyl etc., with propargyl being preferred.

The compounds of formula I are oils, resins or mainly crystalline solids which are stable under normal conditions and have extremely valuable microbicidal properties. They can be used for example in agriculture or related fields preventively and curatively for controlling phytopathogenic pests, e.g. fungi. The compounds of formula I have an excellent biocidal activity and a broad activity spectrum when applied in wide ranges of concentration and their use poses no problems.

The following groups of compounds are preferred on account of their pronounced biocidal, especially fungicidal, properties:

Group Ia:
Compounds of the formula I, wherein $R_1$ is nitro, $R_2$ is trifluoromethyl, $R_3$ is chlorine, $R_4$ is hydrogen or the $-C(O)-R'$ group, in which $R'$ is $C_1-C_4$alkyl which is unsubstituted or substituted by halogen, $C_1-C_3$alkoxy or $C_1-C_3$alkylthio; $R_5$ is hydrogen, halogen, cyano, thiocyano, $C_1-C_6$alkyl, $C_1-C_3$haloalkyl, $C_1-C_6$alkoxy, $C_1-C_3$haloalkoxy, $C_1-C_3$alkylthio-($C_1-C_3$alkoxy), $C_1-C_3$alkylthio, $C_1-C_3$alkoxy which is substituted by $N(C_1-C_2$alkyl$)_2$, or is $C_3-C_4$alkenyloxy, $C_3-C_4$alkenylthio, $C_1-C_3$alkylsulfonyl, $C_1-C_3$alkylsulfoxyl, $N(C_1-C_3$alkyl$)_2$, or a phenyl or benzyl group which are both unsubstituted or substituted by 1 to 3 identical or different members selected from fluorine, chlorine, bromine, nitro, cyano, methoxy, $C_1-C_4$alkyl, dimethylamino or $CF_3$; and $R_6$ and $R_7$ each independently of the other are hydrogen, halogen, cyano, thiocyano, $C_1-C_6$alkyl, $C_1-C_3$haloalkyl, $C_1-C_6$alkoxy, $C_1-C_3$alkoxy which is substituted by halogen, nitro, $C_1-C_3$alkoxy, $C_1-C_3$alkylthio or $N(C_1-C_4$alkyl$)_2$, or are $C_1-C_4$alkylthio, $C_1-C_3$alkylsulfonyl, $C_1-C_3$alkylsulfoxyl, $C_3-C_4$-alkenyloxy, $C_3-C_4$alkenylthio, $C_3-C_4$alkynyloxy, $C_3-C_4$alkynylthio or $N(C_1-C_3$alkyl$)_2$.

Group Ib:
Compounds of the formula I, wherein $R_1$ is nitro, $R_2$ is trifluoromethyl, $R_3$ is hydrogen, $R_4$ is hydrogen or the $-C(O)R'$ group, in which $R'$ is $C_1-C_4$alkyl which is unsubstituted or substituted by halogen, $C_1-C_3$alkoxy or $C_1-C_3$alkylthio; $R_5$ is hydrogen, halogen, cyano, thiocyano, $C_1-C_6$alkyl, $C_1-C_3$haloalkyl, $C_1-C_6$alkoxy, $C_1-C_3$haloalkoxy, $C_1-C_3$alkylthio-($C_1-C_3$alkoxy), $C_1-C_3$alkylthio, $C_1-C_3$alkoxy which is substituted by $N-(C_1-C_2$alkyl$)_2$, or is $C_3-C_4$alkenyloxy, $C_3-C_4$alkenylthio, $C_1-C_3$alkylsulfonyl, $C_1-C_3$alkylsulfoxyl, $N(C_1-C_3$alkyl$)_2$, or a phenyl or benzyl group which are both unsubstituted or substituted by one to three identical or different members selected from fluorine, chlorine, bromine, nitro, cyano, methoxy, $C_1-C_4$alkyl, dimethylamino or $CF_3$; and $R_6$ and $R_7$ independently of the other are hydrogen, halogen, cyano, thiocyano, $C_1-C_6$alkyl, $C_1-C_3$haloalkyl, $C_1-C_6$alkoxy, $C_1-C_3$alkoxy which is substituted by halogen, nitro, $C_1-C_3$alkoxy, $C_1-C_3$alkylthio or $N(C_1-C_4$alkyl$)_2$, or are $C_1-C_4$alkylthio, $C_1-C_3$alkylsulfonyl, $C_1-C_3$-alkylsulfoxyl, $C_3-C_4$alkenyloxy, $C_3-C_4$alkenylthio, $C_3-C_4$alkynyloxy, $C_3-C_4$alkynylthio or $N(C_1-C_4$alkyl$)_2$.

Group Ic:
Compounds of the formula I, wherein $R_1$ is trifluoromethyl, $R_2$ is nitro, $R_3$ is hydrogen, $R_4$ is hydrogen or the $-C(O)R'$ group, in which $R'$ is $C_1-C_4$alkyl which is unsubstituted or substituted by halogen, $C_1-C_3$alkoxy or $C_1-C_3$alkylthio; $R_5$ is hydrogen, halogen, cyano, thiocyano, $C_1-C_6$alkyl, $C_1-C_3$haloalkyl, $C_1-C_6$alkoxy, $C_1-C_3$haloalkoxy, $C_1-C_3$alkylthio-($C_1-C_3$alkoxy), $C_1$–$C_3$alkylthio, $C_1$–$C_3$alkoxy which is substituted by N-($C_1$–$C_2$alkyl)$_2$, or is $C_3$–$C_4$alkenyloxy, $C_3$–$C_4$alkenylthio, $C_1$–$C_3$alkylsulfonyl, $C_1$–$C_3$alkylsulfoxyl, N($C_1$–$C_3$alkyl)$_2$, or a phenyl or benzyl group which are both unsubstituted or substituted by one to three identical or different members selected from fluorine, chlorine, bromine, nitro, cyano, methoxy, $C_1$–$C_4$alkyl, dimethylamino or $CF_3$; and $R_6$ and $R_7$ independently of the other are hydrogen, halogen, cyano, thiocyano, $C_1$–$C_6$alkyl, $C_1$–$C_3$haloalkyl, $C_1$–$C_6$alkoxy, $C_1$–$C_3$alkoxy which is substituted by halogen, nitro, $C_1$–$C_3$alkoxy, $C_1$–$C_3$alkylthio or N($C_1$–$C_4$alkyl)$_2$, or are $C_1$–$C_4$alkylthio, $C_1$–$C_3$alkylsulfonyl, $C_1$–$C_3$alkylsulfoxyl, $C_3$–$C_4$alkenyloxy, $C_3$–$C_4$alkenylthio, $C_3$–$C_4$alkynyloxy, $C_3$–$C_4$alkynylthio or N($C_1$–$C_3$alkyl)$_2$.

Group Id:
Compounds of formula I, wherein $R_1$ is $NO_2$, $R_2$ is $NO_2$, $R_3$ is hydrogen and the other substituents are as defined in group Ia.

Group Ie:
Compounds of the formula I, wherein $R_1$ is hydrogen, $R_2$ is $CF_3$ or $NO_2$, $R_3$ is hydrogen, and the other substituents are as defined in group Ia.

Group If:
Compounds of the formula I, wherein $R_1$ is $NO_2$ or $CF_3$, $R_2$ is hydrogen, $R_3$ is hydrogen, and the other substituents are as defined in group Ia.

Group Ig:
Compounds of the formula I, wherein $R_1$ is $NO_2$ or $CF_3$, $R_2$ is $NO_2$ or $CF_3$, $R_3$ is hydrogen or halogen, $R_4$ is hydrogen or the —C(O)R' group, in which R' is $C_1$–$C_4$alkyl which is unsubstituted or substituted by halogen, $C_1$–$C_3$alkoxy or $C_1$–$C_3$alkylthio; $R_5$, $R_6$ and $R_7$ are each independently hydrogen, halogen, nitro, cyano, thiocyano, mercapto, $C_1$–$C_6$alkyl, $C_1$–$C_6$haloalkyl, $C_1$–$C_6$alkoxy, $C_1$–$C_6$alkoxy which is substituted by halogen, nitro, cyano, $C_1$–$C_3$alkoxy, $C_1$–$C_3$alkylthio and/or N($C_1$–$C_4$alkyl)$_2$, or are $C_3$–$C_6$cycloalkoxy, $C_3$–$C_6$alkenyloxy, $C_3$–$C_6$alkynyloxy, $C_1$–$C_6$alkylthio, $C_3$–$C_6$alkenylthio, $C_1$–$C_6$alkylsulfonyl, $C_1$–$C_6$alkylsulfoxyl or the N($C_1$–$C_4$alkyl)$_2$ group, and $R_5$ can additionally be a phenyl or benzyl group which are both unsubstituted or substituted by 1 to 3 identical or different members selected from halogen, nitro, cyano, $C_1$–$C_4$alkyl, $C_1$–$C_3$haloalkyl, N($C_1$–$C_3$alkyl)$_2$ and/or $C_1$–$C_3$alkoxy.

Within the above subgroups, those compounds are particularly preferred in which the substituent $R_4$ is hydrogen.

Examples of particularly preferred individual compounds are:
N-(3'-chloro-2',6'-dinitro-4'-trifluoromethylphenyl)-5-amino-4-chloro-6-methoxypyrimidine (compound 1.1),
N-(3'-chloro-2',6'-dinitro-4'-trifluoromethylphenyl)-5-amino-4,6-dimethylthiopyrimidine (compound 1.2),
N-(3'-chloro-2',6'-dinitro-4'-trifluoromethylphenyl)-5-amino-4,6-ditrifluoroethoxypyrimidine (compound 1.3),
N-(3'-chloro-2',6'-dinitro-4'-trifluoromethylphenyl)-5-amino-4,6-dichloropyrimidine (compound 1.4),
N-(3'-chloro-2',6'-dinitro-4'-trifluoromethylphenyl)-5-amino-4-chloro-6-methylmercaptopyrimidine (compound 1.184),
N-(3'-chloro-2',6'-dinitro-4'-trifluoromethylphenyl)-5-amino-4-chloro-2-methyl-6-methoxypyrimidine (compound 1.205),
N-(3-chloro-2',6'-dinitro-4'-trifluoromethylphenyl)-5-amino-2-chloro-4-methoxypyrimidine (compound 1.51),
N-(3'-chloro-2',6'-dinitro-4'-trifluoromethylphenyl)-5-amino-2,4-dichloropyrimidine (compound 1.49),
N-(3'-chloro-2',6'-dinitro-4'-trifluoromethylphenyl)-5-amino-2-chloro-4-allyloxypyrimidine (compound 1.210),
N-(3'-chloro-2',6'-dinitro-4'-trifluoromethylphenyl)-5-amino-2-chloro-4-allylmercaptopyrimidine (compound 1.57),
N-(3'-chloro-2',6'-dinitro-4'-trifluoromethylphenyl)-5-amino-2-chloro-4-propargyloxypyrimidine (compound 1.211),
N-(3'-chloro-2',6'-dinitro-4'-trifluoromethylphenyl)-5-amino-4,6-dichloro-2-methylpyrimidine (compound 1.96),
N-(3'-chloro-2',6'-dinitro-4'-trifluoromethylphenyl)-5-amino-4,6-dichloro-2-phenylpyrimidine (compound 1.125),
N-(2',6'-dinitro-4'-trifluoromethylphenyl)-5-amino-4,6-dichloropyrimidine (compound 2.4),
N-(2',4-dinitro-6'-trifluoromethylphenyl)-5-amino-4,6-dichloropyrimidine (compound 3.4),
N-(2',4',6'-trinitrophenyl)-5-amino-4,6-dichloropyrimidine (compound 7.1),
N-(2'-nitro-4'-trifluoromethylphenyl)-5-amino-4,6-dichloropyrimidine (compound 8.1).

The compounds of formula I are prepared by reacting a compound of the formula II

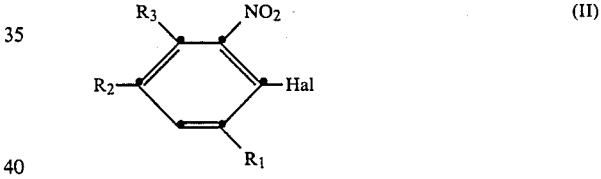

with a pyrimidine derivative of the formula III

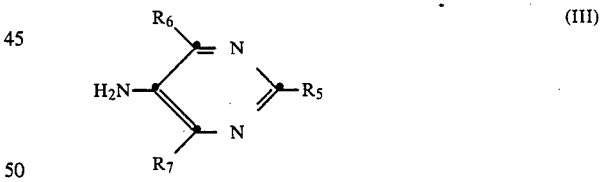

in the presence of a base, to give a compound of the formula I'

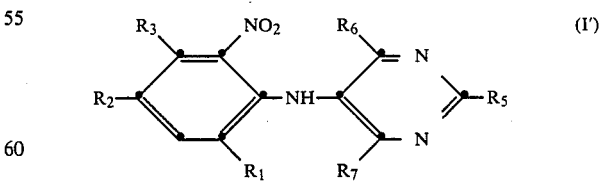

and, to obtain an N-acylated derivative, N-acylating the compound of the formula I' with a reactive derivative of the carboxylic acid of the formula IV $R_7COOH$ (IV)

in which formulae above the substituents $R_1$ to $R_7$ are as defined for formula I and Hal is halogen, preferably chlorine or bromine.

The following reaction conditions are advantageous for the preparation of the compounds of formula I and-/or I':

The N-alkylation of (II) with (III) to give (I') and the N-acylation of (I') with (IV) to give (I) take place with dehydrohalogenation.

The reaction temperature of the N-alkylation is in the range from $-60°$ to $+150°$ C., preferably from $-50°$ to $+30°$ C., and that for the N-acylation is in the range from 0° to 180° C., preferably from 0° to $+150°$ C. or at the boiling point of the solvent or solvent mixture. In both reactions it is convenient to use an acid acceptor or a condensing agent. Examples of suitable acid acceptors or condensing agents are organic and inorganic bases, e.g. tertiary amines such as trialkylamines (trimethylamine, triethylamine, tripropylamine etc.), pyridine and pyridine bases (4-dimethylaminopyridine, 4-pyrrolidylaminopyridine etc.), oxides, hydroxides, carbonates and bicarbonates of alkali metals and alkaline earth metals, as well as alkali metal acetates.

The reactions may be conducted in the presence of inert solvents or diluents. Examples of suitable solvents and diluents are: aliphatic and aromatic hydrocarbons such as benzene, toluene, xylenes, petroleum ether; halogenated hydrocarbons such as chlorobenzene, methylene chloride, ethylene chloride, chloroform, carbon tetrachloride, tetrachloroethylene; ethers and ethereal compounds such as dialkyl ethers (diethyl ether, diisopropyl ether, tert-butylmethyl ether etc.), anisole, dioxan, tetrahydrofuran; nitriles such as acetonitrile and propionitrile; N,N-dialkylated amides such as dimethylformamide; dimethylsulfoxide; ketones such as acetone, diethyl ketone, methyl ethyl ketone; and mixtures of such solvents. In some cases the acylating or alkylating agent itself may be used as solvent. The presence of a catalyst such as dimethylformamide can be advantageous.

The reaction of (II) with (III) can also be carried out in an aqueous two-phase system in accordance with the generally known principle of phase transfer catalysis.

The following solvents for example are suitable for the organic water-immiscible phase: aliphatic and aromatic hydrocarbons such as pentane, hexane, cyclohexane, petroleum ether, ligroin, benzene, toluene, xylenes etc.; halogenated hydrocarbons such as dichloromethane, chloroform, carbon tetrachloride, ethylene dichloride, 1,2-dichloroethane, tetrachloroethylene and the like, or aliphatic ethers such as diethyl ether, diisopropyl ether, tert-butylmethyl ether etc.

Examples of suitable phase transfer catalysts are: tetraalkylammonium halides, hydrogen sulfates or hydroxides, e.g. tetrabutylammonium chloride, tetrabutylammonium bromide, tetrabutylammonium iodide, triethylbenzylammonium chloride or triethylbenzylammonium bromide, tetrapropylammonium chloride, tetrapropylammonium bromide or tetrapropylammonium iodide etc. Suitable phase transfer catalysts are also phosphonium salts. The reaction temperatures are generally in the range from $-30°$ to 130° C. or may also be at the boiling point of the solvent or mixture of solvents.

Unless otherwise expressly specified, one or more inert solvents or diluents may be present in the preparation of all starting materials, intermediates and final products mentioned herein. Examples of suitable inert solvents or diluents are: aliphatic and aromatic hydrocarbons such as benzene, toluene, xylenes, petroleum ether; halogenated hydrocarbons such as chlorobenzene, methylene chloride, ethylene chloride, chloroform, carbon tetrachloride, tetrachloroethylene; ethers and ethereal compounds such as dialkyl ethers (diethyl ether, diisopropyl ether, tert-butylmethyl ether etc.), anisole, dioxan, tetrahydrofuran; nitriles such as acetonitrile, propionitrile; N,N-dialkylated amides such as dimethyl formamide; dimethylsulfoxide; ketones such as acetone, diethyl ketone, methyl ethyl ketone; and mixtures of such solvents with each other. It can often be convenient to carry out the reaction, or partial steps of a reaction, under an inert gas atmosphere and/or in absolute solvents. Suitable inert gases are nitrogen, helium, argon etc.

The starting compounds of the formula II are generally known or they can be prepared by methods known per se. Pyrimidines of the formula II are known from textbooks, e.g. D. J. Brown, "The Pyrimidines", in Heterocyclic Compounds, or they can be prepared by methods analogous to those described therein.

The above described preparatory process, including all partial steps, constitutes an important object of the present invention.

Surprisingly, it has been found that the compounds of formula I have for practical purposes a very useful biocidal spectrum against fungi and bacteria, especially against phytopathogenic fungi and bacteria. They have very advantageous curative, systemic and, in particular, preventive properties, and can be used for protecting numerous cultivated plants. With the compounds of formula I it is possible to inhibit or destroy the microorganisms which occur in plants or parts of plants (fruit, blossoms, leaves, stems, tubers, roots) in different crops of useful plants, while at the same time the parts of plants which grow later are also protected from attack by phytopathogenic micro-organisms and insects.

As microbicides, the compounds of formula I are effective against the phytopathogenic fungi belonging to the following classes: Fungi imperfecti (e.g. Botrytis, Helminthosporium, Fusarium, Septoria, Cercospora and Alternaria); Basidiomycetes (e.g. of the genera Hemileia, Rhizocotonia, Puccinia); and, in particular, against the class of the Ascomycetes (e.g. Venturia, Podosphaera, Erysiphe, Monilinia, Uncinula). In addition, the compounds of formula I have a systemic action. They can also be used as seed dressing agents for protecting seeds (fruit, tubers, grains) and plant cuttings against fungus infections as well as against phytopathogenic fungi which occur in the soil.

Accordingly, the invention also relates to pesticidal compositions, especially fungicidal compositions, and to the use thereof in agricultural or related fields.

The invention further embraces the preparation of such compositions, which comprises homogeneously mixing the active ingredient with one or more compounds or groups of compounds described herein. The invention furthermore relates to a method of treating plants, which comprises applying thereto the compounds of the formula I or the novel compositions.

Target crops to be protected within the scope of the present invention comprise e.g. the following species of plants: cereals (wheat, barley, rye, oats, rice, sorghum and related crops), beet (sugar beet and fodder beet), drupes, pomes and soft fruit (apples, pears, plums, peaches, almonds, cherries, strawberries, rasberries and blackberries), leguminous plants (beans, lentils, peas, soybeans), oil plants (rape, mustard, poppy, olives, sunflowers, coconuts, castor oil plants, cocoa beans, groundnuts), cucumber plants (cucumber, marrows, melons) fibre plants (cotton, flax, hemp, jute), citrus fruit (oranges, lemons, grapefruit, mandarins), vegetables (spinach, lettuce, asparagus, cabbages, carrots, onions, tomatoes, potatoes, paprika), lauraceae (avocados, cinnamon, camphor), or plants such as maize, tobacco, nuts, coffee, sugar cane, tea, vines, hops, bananas and natural rubber plants, as well as ornamentals (composites).

The compounds of formula I are normally applied in the form of compositions and can be applied to the crop area or plant to be treated, simultaneously or in succession, with further compounds. These further compounds can be both fertilisers or micronutrient donors or other preparations that influence plant growth. They can also be selective herbicides, insecticides, fungicides, bactericides, nematicides, mollusicides or mixtures of several of these preparations, if desired together with further carriers, surfactants or application promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilisers.

A preferred method of applying a compound of the formula I, or an agrochemical composition which contains at least one of said compounds, is foliar application. The number of applications and the rate of application depend on the risk of infestation by the corresponding pathogen (type of fungus). However, the compound of formula I can also penetrate the plant through the roots via the soil (systemic action) by impregnating the locus of the plant with a liquid composition, or by applying the compounds in solid form to the soil, e.g. in granular form (soil application). The compounds of formula I may also be applied to seeds (coating) by impregnating the seeds either with a liquid formulation containing a compound of the formula I, or coating them with a solid formulation. In special cases, further types of application are also possible, e.g. selective treatment of the plant stems or buds.

The compounds of the formula I are used in unmodified form or, preferably, together with the adjuvants conventionally employed in the art of formulation, and are therefore formulated in known manner to emulsifiable concentrates, coatable pastes, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering or pouring, are chosen in accordance with the intended objectives and the prevailing circumstances. Advantageous rates of application are normally from 50 g to 5 kg of active ingredient (a.i.) per hectare, preferably from 100 g to 2 kg a.i./ha, most preferably from 200 g to 600 g a.i./ha.

The formulations, i.e. the compositions or preparations containing the compound (active ingredient) of the formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol monomethyl or monoethyl ether, ketones such as cyclohexanone, strongly polar solvents such as N-methyl-2-pyrrolidone, dimethylsulfoxide or dimethylformamide, as well as epoxidised vegetable oils such as epoxidised coconut oil or soybean oil; or water.

The solid carriers used e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues. Particularly advantageous application promoting adjuvants which are able to reduce substantially the rate of application are also natural (animal or vegetable) or synthetic phospholipids of the series of the cephalins and lecithins, e.g. phosphatidyl ethanolamine, phosphatidyl serine, phosphatidyl choline, sphingomyeline, phosphatidyl inisotol, phosphatidyl glycerol, lysolecithin, plasmalogenes or cardiolipin, which can be obtained e.g. from animal or plant cells, in particular from the brain, heart, liver, egg yokes or soya beans. Examples of useful physical forms are phosphatidyl choline mixtures. Examples of synthetic phospholipids are dioctanoylphosphatidyl choline and dipalmitoylphosphatidyl choline.

Depending on the nature of the compound of the formula I to be formulated, suitable surface-active compounds are nonionic, cationic and/or anionic sufactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediamine propylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxyethoxyethanol. Fatty acid esters of polyoxyethylene sorbitan and polyoxyethylene sorbitan trioleate are also suitable non-ionic surfactants.

Cationic surfactants are preferably quaternary ammonium salts which contain, as N-substituent, at least one $C_8$-$C_{22}$alkyl radical and, as further substituents, lower unsubstituted or halogenated alkyl, benzyl or lower hydroxyalkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in "McCutcheon's Detergents and Emulsifiers Annual", MC Publishing Corp. Ridgewood, N.J. 1981; Helmut Stache "Tensid-Taschenbuch", Carl Hanser-Verlag Munich/Vienna 1981.

The agrochemical compositions usually contain 0.1 to 99%, preferably 0.1 to 95%, of a compound of the formula I, 99.9 to 1%, preferably 99.8 to 5%, of a solid or liquid adjuvant, and 0 to 25%, preferably 0.1 to 25%, of a surfactant.

Whereas commercial products are preferably formulated as concentrates, the end user will normally employ dilute formulations.

The compositions may also contain further ingredients such as stabilisers, antifoams, viscosity regulators, binders, tackifiers as well as fertilisers or other compounds for obtaining special effects.

Such agrochemical compositions also constitute an object of the present invention.

The invention is illustrated in more detail by the following Examples, without implying any restriction to what is described therein. Parts and percentages are by weight.

·PREPARATORY EXAMPLES

Example P1: Preparation of (compound 1.1)

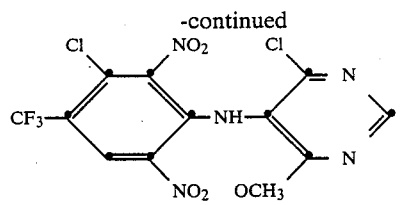

N-(3'-Chloro-2',6'-dinitro-4'-trifluoromethylphenyl)-5-amino-4-chloro-6-methoxypyrimidine 2.84 g (17.8 mmoles) of 5-amino-4-chloro-6-methoxypyrimidine are dissolved in 20 ml of dimethylsulfoxide. With stirring, a solution of 6.24 g (20.5 mmoles) of 1,3-dichloro-2,6-dinitro-4-trifluoromethylbenzene in 15 ml of dimethylsulfoxide and a solution of 2.30 g (20.5 mmoles) of potassium tert-butylate in 15 ml of dimethylsulfoxide are added simultaneously dropwise at 15° C. The dark red solution so obtained is stirred for 1 hour at 15°-20° C. and then poured into ice-water, neutralised with acetic acid and extracted three time with chloroform. The extracts are dried over sodium sulfate and the solvent is removed by rotary evaporation, affording 7.9 g of an oil. This crude product is purified by chromatography through a column of silica gel affording 3.19 g of a crystalline product. Recrystallisation from a mixture of 2 ml of toluene and 8 ml of cyclohexane yields 2.52 g of yellow crystals of m.p. 114°–116° C.

Example P2: Preparation of (compound 1.2)

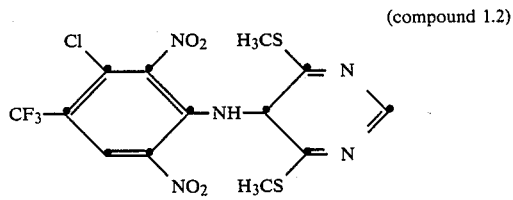

N-(3'-Chloro-2',6'-dinitro-4'-trifluoromethylphenyl)-5-amino-4,6-dimethylthiopyrimidine 7.32 g (0.24 mmole) of 1,3-dichloro-2,6-dinitro-4-trifluoromethylbenzene are dissolved in 30 ml of dimethylsulfoxide and then a solution of 3.75 g (20 mmoles) of 5-amino-4,6-dimethylthiopyrimidine in 20 ml of dimethylsulfoxide and a solution of 2.69 g of potassium tert-butylate in 20 ml of dimethylsulfoxide are added simultaneously dropwise at 15° C. with cooling. The reaction solution is stirred for 15 hours at 20° C. and then poured into ice-water and, after neutralisation with acetic acid, extracted three times with chloroform. The extracts are washed with water, dried over sodium sulfate, and the chloroform is removed, affording 10.7 g of a yellow oil. The crude product is purified by chromatography through a column of silica gel, affording 2.04 g of starting 5-amino-4,6-di(methylmercapto)pyrimidine and 2.8 g of a yellow product which is recrystallised from 1 ml of toluene and 5 ml of cyclohexane to give 2.03 g of compound 1.2 of m.p. 146°–147° C.

Example P3: Preparation of (compound 1.3)

-continued

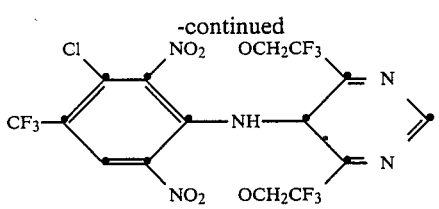

N-(3'-Chloro-2',6'-dinitro-4'-trifluoromethylphenyl)-5-amino-4,6-ditrifluoroethoxyprimidine 3.36 g (11 mmoles) of 1,3-dichloro-2,6-dinitro-4-trifluoromethylbenzene are dissolved in 20 ml of dimethylsulfoxide and then a solution of 2.62 g (9 mmoles) of 5-amino-4,6-ditrifluoroethoxypyrimidine in 15 ml of dimethylsulfoxide and a solution of 2.47 g (22 mmoles) of potassium tert-butylate in 15 ml of dimethylsulfoxide are added simultaneously dropwise at 15° C. with cooling. The dark red solution so obtained is stirred for 3 hours at room temperature. It still contains starting pyrimidine. A further 2.0 g (6.9 mmoles) of 1,3-dichloro-2,6-dinitro-4-trifluoromethylbenzene and 1.5 g (13.4 mmoles) of potassium tert-butylate are added. Working up by extraction and column chromatography yields 3.54 g of yellow product. Recrystallisation from 1 ml of toluene and 9 ml of cyclohesane yields 2.00 g of product with a melting point of 97°–99° C.

Example P4: Preparation of

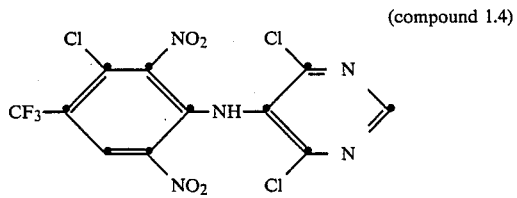

(compound 1.4)

N-(3'-Chloro-2',6'-dinitro-4'-trifluoromethylphenyl)-5-amino-4,6-dichloropyrimidine Following the procedure of Example P3, reaction of 1.64 g of 5-amino-4,6-dichloropyrimidine with 3.05 g of 1,3-dichloro-2,6-dinitro-4-trifluoromethylbenzene, in the presence of 1.67 g of potassium tert-butylate in dimethylsulfoxide, yields 1.81 g of pure product with a melting point of 127°–128° C.

High yields and pure products are obtained by using tetrahydrofuran as solvent instead of dimethylsulfoxide in Examples P1 to P4, and carrying out the reaction in the temperature range from −50° to −30° C.

Example P5: Preparation of

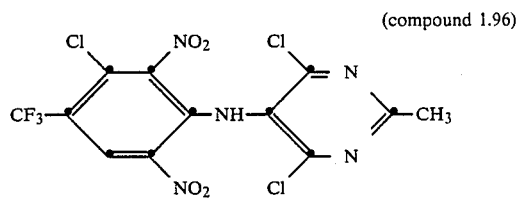

(compound 1.96)

N-(3'-Chloro-2',6'-dinitro-4'-trifluoromethylphenyl)-5-amino-4,6-dichloro-2-methylpyrimidine 6.71 g (0.022 mole) of 1,3-dichloro-2,6-dinitro-4-trifluoromethylbenzene and 3.56 g (0.020 mole) of 5-amino-4,6-dichloro-2-methylpyrimidine are dissolved in 50 ml of tetrahydrofuran. The solution is cooled to −30° C. and, at this temperature, a solution of 4.6 g (0.041 mole) of potassium tert-butylate in 50 ml of tetrahydrofuran is added dropwise. After 1 hour at −30° to 0° C., the mixture is extracted with water and ethyl acetate while adding 10 ml of acetic acid. The extracts are dried over sodium sulfate and concentrated, affording 10.5 g of an oil as crude product. This product is purified by chromatography through a column of silica gel using a mixture of 3 parts of petroleum ether and 1 part of ethyl acetate. The solvent is removed by rotary evaporation, affording 8.3 g of product as residue. Recrystallisation from a mixture of toluene and cyclohexane yields 6.80 g (69.2% of theory) of yellow crystals with a melting point of 134°–136° C.

The following compounds of formula I are prepared by methods analogous to those described in the foregoing Examples:

TABLE 1

Compounds of the formula

| Compound | $R_5$ | $R_6$ | $R_7$ | Physical data [°C.] |
|---|---|---|---|---|
| 1.1 | H | Cl | $OCH_3$ | m.p. 114–116 |
| 1.2 | H | $SCH_3$ | $SCH_3$ | m.p. 146–147 |
| 1.3 | H | $OCH_2CF_3$ | $OCH_2CF_3$ | m.p. 97–99 |
| 1.4 | H | Cl | Cl | m.p. 127–128 |
| 1.5 | Cl | $CH_3$ | $CH_3$ | |
| 1.6 | SCN | $CH_3$ | $CH_3$ | |
| 1.7 | $OCH_2CF_3$ | $CH_3$ | $CH_3$ | |
| 1.8 | $SCH_3$ | $CH_3$ | $CH_3$ | |
| 1.9 | $OC_2H_5$ | $CH_3$ | $CH_3$ | |
| 1.10 | Cl | $CF_3$ | $CF_3$ | |
| 1.11 | $OC_4H_9-n$ | $CF_3$ | $CF_3$ | |
| 1.12 | $SCH_2CH=CH_2$ | $CF_3$ | $CF_3$ | |
| 1.13 | F | $CF_3$ | $CF_3$ | |
| 1.14 | $OCH(CH_3)_2$ | $CCl_3$ | $CCl_3$ | |
| 1.15 | Cl | H | $CH_3$ | |

TABLE 1-continued

Compounds of the formula

[Structure: dinitro-chloro-trifluoromethyl-phenyl-NH linked to pyrimidine ring with R6, R7, R5 substituents]

| Compound | R5 | R6 | R7 | Physical data [°C.] |
|---|---|---|---|---|
| 1.16 | Br | H | CH3 | |
| 1.17 | OC2H5 | H | C2H5 | |
| 1.18 | SCN | H | CH3 | |
| 1.19 | Cl | H | H | m.p. 152–154 |
| 1.20 | OCH2CH2F | H | H | |
| 1.21 | O(CH2)3N(C2H5)2 | H | H | |
| 1.22 | N(CH3)2 | H | H | |
| 1.23 | O(CH2)2SC2H5 | H | H | |
| 1.24 | Cl | Cl | Cl | |
| 1.25 | Cl | Cl | OC2H5 | |
| 1.26 | Cl | Cl | SC2H5 | |
| 1.27 | Cl | Cl | OCH2CF3 | |
| 1.28 | Cl | OCH3 | OCH3 | |
| 1.29 | Cl | OCH(CF3)2 | OCH(CF3)2 | |
| 1.30 | Cl | SCH3 | SCH3 | |
| 1.31 | Cl | Cl | OCH2CH2OCH3 | |
| 1.32 | Cl | Cl | OCH2CH2CH2Cl | |
| 1.33 | OCH2CF3 | OCH2CF3 | OCH2CF3 | |
| 1.34 | F | F | F | |
| 1.35 | Cl | Cl | OC6H13—n | |
| 1.36 | Cl | Cl | SC4H9—n | |
| 1.37 | Cl | Cl | OCH2CH=CH2 | |
| 1.38 | Cl | Cl | OCH2C≡CH | |
| 1.39 | Cl | OCH2CH=CH2 | O—cyclopentyl | |
| 1.40 | Br | Br | Br | |
| 1.41 | Br | OC2H5 | SCH2CH=CH2 | |
| 1.42 | F | OC4H9—n | OC4H9—n | |
| 1.43 | Cl | OCH2CH2NO2 | OCH2CH2NO2 | |
| 1.44 | Cl | Cl | O(CH2)3OC3H7—n | |
| 1.45 | Cl | O(CH2)3N(CH3)2 | O(CH2)3N(CH3)2 | |
| 1.46 | OC6H11—n | OC6H11—n | OC6H11—n | |
| 1.47 | Cl | Cl | SOCH3 | |
| 1.48 | Cl | Cl | SO2C2H5 | |
| 1.49 | Cl | H | Cl | m.p. 125–126 |
| 1.50 | F | H | F | |
| 1.51 | Cl | H | OCH3 | m.p. 156–157 |
| 1.52 | Cl | H | OC2H5 | |
| 1.53 | Cl | H | OCH2CF3 | |
| 1.54 | Cl | H | OCH2CH2OCH3 | |
| 1.55 | Cl | H | OCH(CH3)2 | |
| 1.56 | Cl | H | SC2H5 | |
| 1.57 | Cl | H | SCH2CH=CH2 | m.p. 145–146 |
| 1.58 | Cl | H | SO2CH3 | |
| 159 | Cl | H | SCN | |
| 1.60 | Cl | H | SC4H9—t | |
| 1.61 | Cl | H | O(CH2)3Cl | |
| 1.62 | F | H | SCH3 | |
| 1.63 | F | H | OCH3 | |
| 1.64 | Br | H | Br | |
| 1.65 | Br | H | SCH3 | |
| 1.66 | Cl | H | CN | |
| 1.67 | SCH3 | H | SCH3 | |
| 1.68 | SH | H | SH | |
| 1.69 | OCH3 | H | Cl | |
| 1.70 | SC2H5 | H | Cl | |
| 1.71 | OCH2CF3 | H | Cl | |
| 1.72 | Cl | H | O(CH2)3N(CH3)2 | |
| 1.73 | Cl | H | O(CH2)2OC3H7—n | |
| 1.74 | Cl | H | OC6H11—n | |
| 1.75 | OC6H11—n | H | Cl | |
| 1.76 | OCH2CH=CH2 | H | SCH(CH3)2 | |
| 1.77 | Cl | H | SO2C2H5 | |
| 1.78 | Cl | CH3 | Cl | m.p. 154–156 |
| 1.79 | Cl | CH3 | OCH3 | |
| 1.80 | Cl | CH3 | SC2H5 | |
| 1.81 | Cl | CH3 | OCH2CCl3 | |
| 1.82 | Cl | CH3 | OCH2C≡CH | |
| 1.83 | SCH3 | CH3 | SCH3 | |
| 1.84 | OCH(CH3)2 | CH3 | SC2H5 | |

TABLE 1-continued

Compounds of the formula $$\text{Cl, CF}_3, \text{NO}_2 \text{ benzene-NH-C(R}_6\text{)=C(R}_7\text{)- pyrimidine with R}_5$$

| Compound | $R_5$ | $R_6$ | $R_7$ | Physical data [°C.] |
|---|---|---|---|---|
| 1.85 | Cl | $CH_3$ | CN | |
| 1.86 | Cl | $CF_3$ | Cl | |
| 1.87 | Cl | $CF_3$ | $SCH_3$ | |
| 1.88 | Cl | $CF_3$ | $OCH_3$ | |
| 1.89 | Cl | $CCl_3$ | $SC_2H_5$ | |
| 1.90 | Cl | $CCl_3$ | $OC_4H_9-t$ | |
| 1.91 | Cl | $CCl_3$ | $OCH_2CF_3$ | |
| 1.92 | Cl | $CCl_3$ | $OCH_2CH_2OCH_3$ | |
| 1.93 | Cl | $CCl_3$ | SCN | |
| 1.94 | Cl | $CCl_3$ | $OC_6H_{13}-n$ | |
| 1.95 | $SO_2CH_3$ | $CH_3$ | $SO_2CH_3$ | |
| 1.96 | $CH_3$ | Cl | Cl | m.p. 134–136 |
| 1.97 | $C_2H_5$ | F | F | |
| 1.98 | $C_6H_{11}-n$ | Cl | $OCH_3$ | |
| 1.99 | $(CH_3)_2CH$ | Cl | $OC_2H_5$ | |
| 1.100 | $CH_3$ | Cl | $SCH_3$ | |
| 1.101 | $CH_3$ | Cl | $S-C_4H_9-t$ | |
| 1.102 | $CH_3$ | Cl | $SCH_2CH=CH_2$ | |
| 1.103 | $CH_3$ | Cl | SCN | |
| 1.104 | $C_2H_5$ | Cl | O—cyclohexyl | |
| 1.105 | $C_3H_7-n$ | Cl | $O(CH_2)_3Cl$ | |
| 1.106 | $C_4H_9-n$ | Cl | $O(CH_2)_2OC_2H_5$ | |
| 1.107 | $CCl_3$ | Cl | $OCH_3$ | |
| 1.108 | $CCl_3$ | Cl | $OC_2H_5$ | |
| 1.109 | $CCl_3$ | Cl | $SC_2H_5$ | |
| 1.110 | $CCl_3$ | Cl | Cl | m.p. 141–143 |
| 1.111 | $CF_3$ | Cl | Cl | |
| 1.112 | $CF_3$ | Cl | $OCH_3$ | |
| 1.113 | $CF_3$ | $SCH_3$ | $SCH_3$ | |
| 1.114 | $CF_3$ | Cl | $OCH_2CF_3$ | |
| 1.115 | $CH_3$ | $OCH_3$ | $O(CH_2)_3NH_2$ | |
| 1.116 | $CH_3$ | $SC_2H_5$ | $O(CH_2)_3Cl$ | |
| 1.117 | $CH_3$ | $SCH_2CH=CH_2$ | $S-C_4H_9-n$ | |
| 1.118 | $C_2H_5$ | $OCH_2CH_2NO_2$ | $OCH(CF_3)_2$ | |
| 1.119 | $CH_3$ | Br | Br | |
| 1.120 | $CH_3$ | Br | O—cyclopentyl | |
| 1.121 | $CH_2C_6H_5$ | Cl | Cl | |
| 1.122 | $CH_2C_6H_4Cl(4)$ | Cl | $SCH_3$ | |
| 1.123 | $CH_2C_6H_4(OCH_3)(4)$ | Cl | $OC_2H_5$ | |
| 1.124 | $CH_2C_6H_4(NO_2)(4)$ | Cl | Cl | |
| 1.125 | $C_6H_5$ | Cl | Cl | m.p. 170–171 |
| 1.126 | $C_6H_5$ | Cl | $OCH_3$ | m.p. 207–208 |
| 1.127 | $C_6H_5$ | $SCH_3$ | $SCH_3$ | m.p. 276 |
| 1.128 | $C_6H_5$ | Cl | $N(CH_3)_2$ | |
| 1.129 | $C_6H_4Cl(2)$ | Cl | Cl | |
| 1.130 | $C_6H_4Cl(2)$ | Cl | Cl | |
| 1.131 | $C_6H_4Cl(3)$ | Cl | $SC_2H_5$ | |
| 1.132 | $C_6H_4Cl(3)$ | Cl | $N(C_4H_9)_2$ | |
| 1.133 | $C_6H_4Cl(3)$ | Cl | $O(CH_2)_3Cl$ | |
| 1.134 | $C_6H_4Cl(4)$ | $SCH_3$ | $SCH_3$ | |
| 1.135 | $C_6H_4Cl(4)$ | $OCH_3$ | $OC_2H_5$ | |
| 1.136 | $C_6H_4Cl(4)$ | Cl | $OC_6H_{11}-n$ | |
| 1.137 | $C_6H_4CN(4)$ | Cl | $OCH_3$ | |
| 1.138 | $C_6H_4F(3)$ | Cl | Cl | |
| 1.139 | $C_6H_4F(4)$ | Cl | $SCH_3$ | |
| 1.140 | $C_6H_4(OCH_3)(2)$ | Cl | Cl | |
| 1.141 | $C_6H_4(OCH_3)(3)$ | $SC_3H_7-n$ | $C_4H_9-t$ | |
| 1.142 | $C_6H_4(NO_2)(4)$ | Cl | $OC_6H_{11}-n$ | |
| 1.143 | $C_6H_4[N(CH_3)_2](4)$ | Cl | Cl | |
| 1.144 | $C_6H_4(CF_3)(3)$ | Cl | Cl | |
| 1.145 | $C_6H_4(CF_3)(3)$ | Cl | $OCH_3$ | |
| 1.146 | $C_6H_4(CF_3)(4)$ | Cl | $SCH_3$ | |
| 1.147 | $C_6H_3Cl_2(2,4)$ | Cl | Cl | |
| 1.148 | $C_6H_3(NO_2)_2(3,5)$ | Cl | $OC_2H_5$ | |
| 1.149 | $C_6H_3Cl_2(2,4)$ | Cl | $OC_2H_5$ | |
| 1.150 | $C_6H_3(NO_2)(3,5)$ | Cl | Cl | |
| 1.151 | $C_6H_4(CH_3)(4)$ | Cl | Cl | m.p. 159–161 |
| 1.152 | $C_6H_4(CH_3)(4)$ | Cl | $SCH_2CH=CH_2$ | |
| 1.153 | $C_6H_4(C_4H_9-t)(4)$ | Cl | Cl | |

TABLE 1-continued

Compounds of the formula $$\text{structure with Cl, NO}_2, \text{CF}_3, \text{NO}_2 \text{ on benzene ring, NH linked to C=N-C(R}_5\text{)=N-C with R}_6, R_7$$

| Compound | $R_5$ | $R_6$ | $R_7$ | Physical data [°C.] |
|---|---|---|---|---|
| 1.154 | SCH$_3$ | H | OC$_3$H$_7$—n | |
| 1.155 | SCH$_3$ | H | O(CH$_2$)$_2$OCH$_3$ | |
| 1.156 | SCH$_3$ | H | O(CH$_2$)$_3$N(C$_2$H$_5$)$_2$ | |
| 1.157 | N(CH$_3$)$_2$ | H | Cl | |
| 1.158 | N(C$_2$H$_5$)$_2$ | H | OC$_2$H$_5$ | |
| 1.159 | N(CH$_3$)$_2$ | H | O(CH$_2$)$_3$Cl | |
| 1.160 | C$_6$H$_5$ | H | Cl | |
| 1.161 | C$_6$H$_5$ | H | SC$_2$H$_5$ | |
| 1.162 | CH$_3$ | Cl | CH$_3$ | |
| 1.163 | CH$_2$C$_6$H$_5$ | OCH$_3$ | CH$_3$ | |
| 1.164 | C$_6$H$_5$ | Cl | CH$_3$ | |
| 1.165 | SCH$_3$ | OCH$_2$CF$_3$ | CF$_3$ | |
| 1.166 | CH$_3$ | CH$_3$ | CH$_3$ | |
| 1.167 | C$_5$H$_{11}$—n | CH$_3$ | CH$_3$ | |
| 1.168 | C$_6$H$_4$(4) | CF$_3$ | CF$_3$ | |
| 1.169 | C$_6$H$_4$CN(3) | CF$_3$ | CF$_3$ | |
| 1.170 | N(CH$_3$)$_2$ | CH$_3$ | CH$_3$ | |
| 1.171 | SCH$_3$ | H | CH$_3$ | |
| 1.172 | C$_2$H$_5$ | H | CH$_3$ | |
| 1.173 | C$_6$H$_4$Cl(2) | H | CH$_3$ | |
| 1.174 | CH$_3$ | H | H | m.p. 144–145 |
| 1.175 | SCH$_3$ | H | H | |
| 1.176 | C$_6$H$_4$(CF$_3$)(4) | H | H | |
| 1.177 | C$_6$H$_4$(OCH$_3$)(3) | H | H | |
| 1.178 | H | Cl | OC$_2$H$_5$ | m.p. 119–120 |
| 1.179 | H | Cl | OCH(CH$_3$)C$_2$H$_5$ | |
| 1.180 | H | Cl | O—cyclohexyl | |
| 1.181 | H | Cl | OCH$_2$CF$_3$ | |
| 1.182 | H | Cl | OCH$_2$CH=CH$_2$ | m.p. 94–95 |
| 1.183 | H | Cl | OCH$_2$CH$_2$OCH$_3$ | |
| 1.184 | H | Cl | SCH$_3$ | m.p. 140–142 |
| 1.185 | H | N(CH$_3$)$_2$ | SCH$_3$ | |
| 1.186 | H | Cl | SCH(CH$_3$)$_2$ | |
| 1.187 | H | Cl | SCN | |
| 1.188 | H | SCN | SCN | |
| 1.189 | H | Cl | S(O)CH$_3$ | |
| 1.190 | H | Cl | SO$_2$CH$_3$ | |
| 1.191 | H | SH | SH | |
| 1.192 | H | F | F | |
| 1.193 | H | OCH(CF$_3$)$_2$ | OCH(CF$_3$)$_2$ | |
| 1.194 | H | Cl | O(CH$_2$)$_3$Cl | |
| 1.195 | H | OCH$_2$CH$_2$NO$_2$ | O(CH$_2$)$_3$OC$_2$H$_5$ | |
| 1.196 | H | Cl | O(CH$_2$)$_2$N(C$_4$H$_9$—n)$_2$ | |
| 1.197 | H | Cl | OCH$_2$CH$_2$NO$_2$ | |
| 1.198 | H | OCH$_3$ | O(CH$_2$)$_3$N(CH$_3$)$_2$ | |
| 1.199 | H | SC$_2$H$_5$ | OCH$_3$ | |
| 1.200 | H | SCH$_2$CH=CH$_2$ | N(C$_4$H$_9$—n)$_2$ | |
| 1.201 | H | N(CH$_3$)$_2$ | N(C$_2$H$_5$)$_2$ | |
| 1.202 | H | F | SCH$_3$ | |
| 1.203 | H | S—C$_4$H$_9$—t | O(CH$_2$)$_2$OC$_4$H$_9$—n | |
| 1.204 | H | Cl | OCH$_2$CH$_2$CN | |
| 1.205 | CH$_3$ | Cl | OCH$_3$ | m.p. 131–132 |
| 1.206 | OCH$_3$ | OCH$_3$ | H | m.p. 144–145 |
| 1.207 | Cl | N(C$_2$H$_5$)$_2$ | H | m.p. 205 |
| 1.208 | OCH(CH$_3$)$_2$ | H | OCH(CH$_3$)$_2$ | oil |
| 1.209 | OCH$_2$CH$_2$OCH(CH$_3$)$_2$ | H | OCH$_2$CH$_2$OCH(CH$_3$)$_2$ | oil |
| 1.210 | Cl | OCH$_2$CH=CH$_2$ | H | m.p. 147–148 |
| 1.211 | Cl | OCH$_2$C≡CH | H | m.p. 149–150 |
| 1.212 | H | H | H | m.p. 172–173 |
| 1.213 | CH$_3$ | Cl | OC$_2$H$_5$ | m.p. 164–165 |
| 1.214 | Cl | H | SCH$_3$ | m.p. 186–187 |
| 1.215 | H | OCH$_3$ | H | m.p. 120–122 |
| 1.216 | CH$_3$ | Cl | H | m.p. 115–116 |
| 1.217 | CH$_3$ | OC$_2$H$_5$ | H | m.p. 104–106 |
| 1.218 | H | OCH$_3$ | OCH$_3$ | m.p. 137–138 |
| 1.219 | CH$_3$ | SCH$_3$ | H | m.p. 168–170 |
| 1.220 | C$_2$H$_5$ | Cl | Cl | m.p. 154 |
| 1.221 | Cl | H | OCH$_2$CH$_2$SC$_2$H$_5$ | |
| 1.222 | Cl | H | OCH$_2$CCl$_2$CF$_3$ | |

TABLE 1-continued

Compounds of the formula

[Structure: 2-Cl, 3-NO₂, 5-NO₂, 4-CF₃ substituted phenyl-NH- linked to a triazine ring bearing R₆, R₇, and =N-R₅]

| Compound | R₅ | R₆ | R₇ | Physical data [°C.] |
|---|---|---|---|---|
| 1.223 | H | Cl | $OCH_2C\equiv CH$ | |
| 1.224 | $CH_3$ | Cl | $OCH_2CF_3$ | |
| 1.225 | $CH_3$ | Cl | $OCH_2CH=CH_2$ | |
| 1.226 | $CH_3$ | Cl | $OCH_2C\equiv CH$ | |
| 1.227 | $C_2H_5$ | Cl | $OCH_3$ | |
| 1.228 | $C_2H_5$ | Cl | $SCH_3$ | |
| 1.229 | $C_2H_5$ | Cl | $OCH_2CH_2CH_3$ | |
| 1.230 | $CH(CH_3)_2$ | Cl | Cl | |
| 1.231 | $CH(CH_3)_2$ | Cl | $OCH_3$ | |
| 1.232 | $CH(CH_3)_2$ | Cl | $SCH_3$ | |
| 1.233 | $OCH_2CH=CH_2$ | Cl | H | |
| 1.234 | Cl | $CH_3$ | $SCH_3$ | |
| 1.235 | Cl | $CH_3$ | $OCH_2CH=CH_2$ | |
| 1.236 | $SCH_3$ | Cl | Cl | |
| 1.237 | $SCH_3$ | Cl | $OCH_3$ | |
| 1.238 | $SCH_3$ | Cl | $SCH_3$ | |
| 1.239 | $SCH_3$ | Cl | $OCH_2CF_3$ | |
| 1.240 | $SCH_3$ | Cl | $OCH_2CH=CH_2$ | |

TABLE 2

Compounds of the formula

[Structure: 3-NO₂, 5-NO₂, 4-CF₃ substituted phenyl-NH- linked to a triazine ring bearing R₆, R₇, and =N-R₅]

| Compound | R₅ | R₆ | R₇ | Physical data [°C.] |
|---|---|---|---|---|
| 2.1 | H | Cl | $OCH_3$ | m.p. 134–135 |
| 2.2 | H | $SCH_3$ | $SCH_3$ | |
| 2.3 | H | $OCH_2CF_3$ | $OCH_2CF_3$ | |
| 2.4 | H | Cl | Cl | m.p. 159–160 |
| 2.5 | Cl | $CH_3$ | $CH_3$ | |
| 2.6 | SCN | $CH_3$ | $CH_3$ | |
| 2.7 | $OCH_2CF_3$ | $CH_3$ | $CH_3$ | |
| 2.8 | $SCH_3$ | $CH_3$ | $CH_3$ | |
| 2.9 | $OC_2H_5$ | $CH_3$ | $CH_3$ | |
| 2.10 | Cl | $CF_3$ | $CF_3$ | |
| 2.11 | $OC_4H_9-n$ | $CF_3$ | $CF_3$ | |
| 2.12 | $SCH_2CH=CH_2$ | $CF_3$ | $CF_3$ | |
| 2.13 | F | $CF_3$ | $CF_3$ | |
| 2.14 | $OCH(CH_3)_2$ | $CCl_3$ | $CCl_3$ | |
| 2.15 | Cl | H | $CH_3$ | |
| 2.16 | Br | H | $CH_3$ | |
| 2.17 | $OC_2H_5$ | H | $C_2H_5$ | |
| 2.18 | SCN | H | $CH_3$ | |
| 2.19 | Cl | H | H | |
| 2.20 | $OCH_2CH_2F$ | H | H | |
| 2.21 | $O(CH_2)_3N(C_2H_5)_2$ | H | H | |
| 2.22 | $N(CH_3)_2$ | H | H | |
| 2.23 | $O(CH_2)_2SC_2H_5$ | H | H | |
| 2.24 | Cl | Cl | Cl | |
| 2.25 | Cl | Cl | $OC_2H_5$ | |
| 2.26 | Cl | Cl | $SC_2H_5$ | |
| 2.27 | Cl | Cl | $OCH_2CF_3$ | |
| 2.28 | Cl | $OCH_3$ | $OCH_3$ | |
| 2.29 | Cl | $OCH(CF_3)_2$ | $OCH(CF_3)_2$ | |
| 2.30 | Cl | $SCH_3$ | $SCH_3$ | |
| 2.31 | Cl | Cl | $OCH_2CH_2OCH_3$ | |
| 2.32 | Cl | Cl | $OCH_2CH_2CH_2Cl$ | |
| 2.33 | $OCH_2CF_3$ | $OCH_2CF_3$ | $OCH_2CF_3$ | |
| 2.34 | F | F | F | |
| 2.35 | Cl | Cl | $OC_6H_{13}-n$ | |

TABLE 2-continued

Compounds of the formula

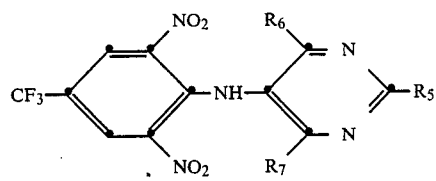

| Compound | $R_5$ | $R_6$ | $R_7$ | Physical data [°C.] |
|---|---|---|---|---|
| 2.36 | Cl | Cl | $SC_4H_9$—n | |
| 2.37 | Cl | Cl | $OCH_2CH=CH_2$ | |
| 2.38 | Cl | Cl | $OCH_2C\equiv CH$ | |
| 2.39 | Cl | $OCH_2CH=CH_2$ | O—cyclopentyl | |
| 2.40 | Br | Br | Br | |
| 2.41 | Br | $OC_2H_5$ | $SCH_2CH=CH_2$ | |
| 2.42 | F | $OC_4H_9$—n | $OC_4H_9$—n | |
| 2.43 | Cl | $OCH_2CH_2NO_2$ | $OCH_2CH_2NO_2$ | |
| 2.44 | Cl | Cl | $O(CH_2)_3OC_3H_7$—n | |
| 2.45 | Cl | $O(CH_2)_3N(CH_3)_2$ | $O(CH_2)_3N(CH_3)_2$ | |
| 2.46 | $OC_6H_{11}$—n | $OC_6H_{11}$—n | $OC_6H_{11}$—n | |
| 2.47 | Cl | Cl | $SOCH_3$ | |
| 2.48 | Cl | Cl | $SO_2C_2H_5$ | |
| 2.49 | Cl | H | Cl | m.p. 116–117 |
| 2.50 | F | H | F | |
| 2.51 | Cl | H | $OCH_3$ | m.p. 145–146 |
| 2.52 | Cl | H | $OC_2H_5$ | |
| 2.53 | Cl | H | $OCH_2CF_3$ | |
| 2.54 | Cl | H | $OCH_2CH_2OCH_3$ | |
| 2.55 | Cl | H | $OCH(CH_3)_2$ | |
| 2.56 | Cl | H | $SC_2H_5$ | |
| 2.57 | Cl | H | $SCH_2CH=CH_2$ | |
| 2.58 | Cl | H | $SO_2CH_3$ | |
| 2.59 | Cl | H | SCN | |
| 2.60 | Cl | H | $SC_4H_9$—t | |
| 2.61 | Cl | H | $O(CH_2)_3Cl$ | |
| 2.62 | F | H | $SCH_3$ | |
| 2.63 | F | H | $OCH_3$ | |
| 2.64 | Br | H | Br | |
| 2.65 | Br | H | $SCH_3$ | |
| 2.66 | Cl | H | CN | |
| 2.67 | $SCH_3$ | H | $SCH_3$ | |
| 2.68 | SH | H | SH | |
| 2.69 | $OCH_3$ | H | Cl | |
| 2.70 | $SC_2H_5$ | H | Cl | |
| 2.71 | $OCH_2CF_3$ | H | Cl | |
| 2.72 | Cl | H | $O(CH_2)_3N(CH_3)_2$ | |
| 2.73 | Cl | H | $O(CH_2)_2OC_3H_7$—n | |
| 2.74 | Cl | H | $OC_6H_{11}$—n | |
| 2.75 | $OC_6H_{11}$—n | H | Cl | |
| 2.76 | $OCH_2CH=CH_2$ | H | $SCH(CH_3)_2$ | |
| 2.77 | Cl | H | $SO_2C_2H_5$ | |
| 2.78 | Cl | $CH_3$ | Cl | |
| 2.79 | Cl | $CH_3$ | $OCH_3$ | |
| 2.80 | Cl | $CH_3$ | $SC_2H_5$ | |
| 2.81 | Cl | $CH_3$ | $OCH_2CCl_3$ | |
| 2.82 | Cl | $CH_3$ | $OCH_2C\equiv CH$ | |
| 2.83 | $SCH_3$ | $CH_3$ | $SCH_3$ | |
| 2.84 | $OCH(CH_3)_2$ | $CH_3$ | $SC_2H_5$ | |
| 2.85 | Cl | $CH_3$ | CN | |
| 2.86 | Cl | $CF_3$ | Cl | |
| 2.87 | Cl | $CF_3$ | $SCH_3$ | |
| 2.88 | Cl | $CF_3$ | $OCH_3$ | |
| 2.89 | Cl | $CCl_3$ | $SC_2H_5$ | |
| 2.90 | Cl | $CCl_3$ | $OC_4H_9$—t | |
| 2.91 | Cl | $CCl_3$ | $OCH_2CF_3$ | |
| 2.92 | Cl | $CCl_3$ | $OCH_2CH_2OCH_3$ | |
| 2.93 | Cl | $CCl_3$ | SCN | |
| 2.94 | Cl | $CCl_3$ | $OC_6H_{13}$—n | |
| 2.95 | $SO_2CH_3$ | $CH_3$ | $SO_2CH_3$ | |
| 2.96 | $CH_3$ | Cl | Cl | m.p.143–144 |
| 2.97 | $C_2H_5$ | F | F | |
| 2.98 | $C_6H_{11}$—n | Cl | $OCH_3$ | |
| 2.99 | $(CH_3)_2CH$ | Cl | $OC_2H_5$ | |
| 2.100 | $CH_3$ | Cl | $SCH_3$ | |
| 2.101 | $CH_3$ | Cl | $S-C_4H_9$—t | |
| 2.102 | $CH_3$ | Cl | $SCH_2CH=CH_2$ | |
| 2.103 | $CH_3$ | Cl | SCN | |
| 2.104 | $C_2H_5$ | Cl | O—cyclohexyl | |
| 2.105 | $C_3H_7$—n | Cl | $O(CH_2)_3Cl$ | |

TABLE 2-continued

Compounds of the formula

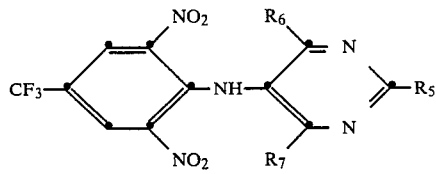

| Compound | R$_5$ | R$_6$ | R$_7$ | Physical data [°C.] |
|---|---|---|---|---|
| 2.106 | C$_4$H$_9$—n | Cl | O(CH$_2$)$_2$OC$_2$H$_5$ | |
| 2.107 | CCl$_3$ | Cl | OCH$_3$ | |
| 2.108 | CCl$_3$ | Cl | OC$_2$H$_5$ | |
| 2.109 | CCl$_3$ | Cl | SC$_2$H$_5$ | |
| 2.110 | CCl$_3$ | Cl | Cl | |
| 2.111 | CF$_3$ | Cl | Cl | |
| 2.112 | CF$_3$ | Cl | OCH$_3$ | |
| 2.113 | CF$_3$ | SCH$_3$ | SCH$_3$ | |
| 2.114 | CF$_3$ | Cl | OCH$_2$CF$_3$ | |
| 2.115 | CH$_3$ | OCH$_3$ | O(CH$_2$)$_3$NH$_2$ | |
| 2.116 | CH$_3$ | SC$_2$H$_5$ | O(CH$_2$)$_3$Cl | |
| 2.117 | CH$_3$ | SCH$_2$CH=CH$_2$ | S—C$_4$H$_9$—n | |
| 2.118 | C$_2$H$_5$ | OCH$_2$CH$_2$NO$_2$ | OCH(CF$_3$)$_2$ | |
| 2.119 | CH$_3$ | Br | Br | |
| 2.120 | CH$_3$ | Br | O—cyclopentyl | |
| 2.121 | CH$_2$C$_6$H$_5$ | Cl | Cl | |
| 2.122 | CH$_2$C$_6$H$_4$Cl(4) | Cl | SCH$_3$ | |
| 2.123 | CH$_2$C$_6$H$_4$(OCH$_3$)(4) | Cl | OC$_2$H$_5$ | |
| 2.124 | CH$_2$C$_6$H$_4$(NO$_2$)(4) | Cl | Cl | |
| 2.125 | C$_6$H$_5$ | Cl | Cl | |
| 2.126 | C$_6$H$_5$ | Cl | OCH$_3$ | |
| 2.127 | C$_6$H$_5$ | Cl | SCH$_3$ | |
| 2.128 | C$_6$H$_5$ | Cl | N(CH$_3$)$_2$ | |
| 2.129 | C$_6$H$_4$Cl(2) | Cl | Cl | |
| 2.130 | C$_6$H$_4$Cl(2) | Cl | Cl | |
| 2.131 | C$_6$H$_4$Cl(3) | Cl | SC$_2$H$_5$ | |
| 2.132 | C$_6$H$_4$Cl(3) | Cl | N(C$_4$H$_9$)$_2$ | |
| 2.133 | C$_6$H$_4$Cl(3) | Cl | O(CH$_2$)$_3$Cl | |
| 2.134 | C$_6$H$_4$Cl(4) | SCH$_3$ | SCH$_3$ | |
| 2.135 | C$_6$H$_4$Cl(4) | OCH$_3$ | OC$_2$H$_5$ | |
| 2.136 | C$_6$H$_4$Cl(4) | Cl | OC$_6$H$_{11}$—n | |
| 2.137 | C$_6$H$_4$CN(4) | Cl | OCH$_3$ | |
| 2.138 | C$_6$H$_4$F(3) | Cl | Cl | |
| 2.139 | C$_6$H$_4$F(4) | Cl | SCH$_3$ | |
| 2.140 | C$_6$H$_4$(OCH$_3$)(2) | Cl | Cl | |
| 2.141 | C$_6$H$_4$(OCH$_3$)(3) | SC$_3$H$_7$—n | C$_4$H$_9$—t | |
| 2.142 | C$_6$H$_4$(NO$_2$)(4) | Cl | OC$_6$H$_{11}$—n | |
| 2.143 | C$_6$H$_4$[N(CH$_3$)$_2$](4) | Cl | Cl | |
| 2.144 | C$_6$H$_4$(CF$_3$)(3) | Cl | Cl | |
| 2.145 | C$_6$H$_4$(CF$_3$)(3) | Cl | OCH$_3$ | |
| 2.146 | C$_6$H$_4$(CF$_3$)(4) | Cl | SCH$_3$ | |
| 2.147 | C$_6$H$_3$Cl$_2$(2,4) | Cl | Cl | |
| 2.148 | C$_6$H$_3$(NO$_2$)$_2$(3,5) | Cl | OC$_2$H$_5$ | |
| 2.149 | C$_6$H$_3$Cl$_2$(2,4) | Cl | OC$_2$H$_5$ | |
| 2.150 | C$_6$H$_3$(NO$_2$)(3,5) | Cl | Cl | |
| 2.151 | C$_6$H$_4$(CH$_3$)(4) | Cl | Cl | |
| 2.152 | C$_6$H$_4$(CH$_3$)(4) | Cl | SCH$_2$CH=CH$_2$ | |
| 2.153 | C$_6$H$_4$(C$_4$H$_9$—t)(4) | Cl | Cl | |
| 2.154 | SCH$_3$ | H | OC$_3$H$_7$—n | |
| 2.155 | SCH$_3$ | H | O(CH$_2$)$_2$OCH$_3$ | |
| 2.156 | SCH$_3$ | H | O(CH$_2$)$_3$N(C$_2$H$_5$)$_2$ | |
| 2.157 | N(CH$_3$)$_2$ | H | Cl | |
| 2.158 | N(C$_2$H$_5$)$_2$ | H | OC$_2$H$_5$ | |
| 2.159 | N(CH$_3$)$_2$ | H | O(CH$_2$)$_3$Cl | |
| 2.160 | C$_6$H$_5$ | H | Cl | |
| 2.161 | C$_6$H$_5$ | H | SC$_2$H$_5$ | |
| 2.162 | CH$_3$ | Cl | CH$_3$ | |
| 2.163 | CH$_2$C$_6$H$_5$ | OCH$_3$ | CH$_3$ | |
| 2.164 | C$_6$H$_5$ | Cl | CH$_3$ | |
| 2.165 | SCH$_3$ | OCH$_2$CF$_3$ | CF$_3$ | |
| 2.166 | CH$_3$ | CH$_3$ | CH$_3$ | |
| 2.167 | C$_5$H$_{11}$—n | CH$_3$ | CH$_3$ | |
| 2.168 | C$_6$H$_4$(4) | CF$_3$ | CF$_3$ | |
| 2.169 | C$_6$H$_4$CN(3) | CF$_3$ | CF$_3$ | |
| 2.170 | N(CH$_3$)$_2$ | CH$_3$ | CH$_3$ | |
| 2.171 | SCH$_3$ | H | CH$_3$ | |
| 2.172 | C$_2$H$_5$ | H | CH$_3$ | |
| 2.173 | C$_6$H$_4$Cl(2) | H | CH$_3$ | |
| 2.174 | CH$_3$ | H | H | m.p. 168–169 |
| 2.175 | SCH$_3$ | H | H | |

TABLE 2-continued
Compounds of the formula

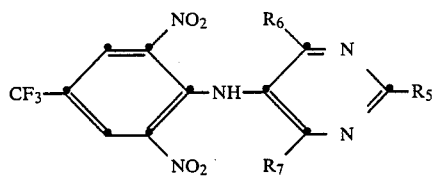

| Compound | R5 | R6 | R7 | Physical data [°C.] |
|---|---|---|---|---|
| 2.176 | C6H4(CF3)(4) | H | H | |
| 2.177 | C6H4(OCH3)(3) | H | H | |
| 2.178 | H | Cl | OC2H5 | |
| 2.179 | H | Cl | OCH(CH3)C2H5 | |
| 2.180 | H | Cl | O—cyclohexyl | |
| 2.181 | H | Cl | OCH2CF3 | |
| 2.182 | H | Cl | OCH2CH=CH2 | m.p. 71–73 |
| 2.183 | H | Cl | OCH2CH2OCH3 | |
| 2.184 | H | Cl | SCH3 | |
| 2.185 | H | Cl | SCH3 | |
| 2.186 | H | Cl | SCH(CH3)2 | |
| 2.187 | H | Cl | SCN | |
| 2.188 | H | SCN | SCN | |
| 2.189 | H | Cl | S(O)CH3 | |
| 2.190 | H | Cl | SO2CH3 | |
| 2.191 | H | SH | SH | |
| 2.192 | H | F | F | |
| 2.193 | H | OCH(CF3)2 | OCH(CF3)2 | |
| 2.194 | H | Cl | O(CH2)3Cl | |
| 2.195 | H | OCH2CH2NO2 | O(CH2)3OC2H5 | |
| 2.196 | H | Cl | O(CH2)2N(C4H9—n)2 | |
| 2.197 | H | Cl | OCH2CH2NO2 | |
| 2.198 | H | OCH3 | O(CH2)3N(CH3)2 | |
| 2.199 | H | SC2H5 | OCH3 | |
| 2.200 | H | SCH2CH=CH2 | N(C4H9—n)2 | |
| 2.201 | H | N(CH3)2 | N(C2H5)2 | |
| 2.202 | H | F | SCH3 | |
| 2.203 | H | S—C4H9—t | O(CH2)2OC4H9—n | |
| 2.204 | H | Cl | OCH2CH2CN | |
| 2.205 | OCH(CH3)2 | OCH(CH3)2 | H | oil |
| 2.206 | OCH2CH2OCH(CH3)2 | H | OCH2CH2OCH(CH3)2 | oil |
| 2.207 | Cl | H | OCH2CH=CH2 | m.p. 74–75 |
| 2.208 | Cl | H | OCH2C≡CH | m.p. 91–92 |
| 2.209 | H | H | H | m.p. 134–135 |
| 2.210 | CH3 | Cl | OC2H5 | m.p. 110–111 |
| 2.211 | CH3 | OCH3 | Cl | m.p. 143–144 |
| 2.212 | C2H5 | Cl | Cl | m.p. 90–91 |
| 2.213 | Cl | H | OCH2CH2SC2H5 | |
| 2.214 | Cl | H | OCH2CCl2CF3 | |
| 2.215 | H | Cl | OCH2C≡CH | |
| 2.216 | CH3 | Cl | OCH2CF3 | |
| 2.217 | CH3 | Cl | OCH2CH=CH2 | |
| 2.218 | CH3 | Cl | OCH2C≡CH | |
| 2.219 | C2H5 | Cl | OCH3 | |
| 2.220 | C2H5 | Cl | SCH3 | |
| 2.221 | C2H5 | Cl | OCH2CH2CH3 | |
| 2.222 | CH(CH3)2 | Cl | Cl | |
| 2.223 | CH(CH3)2 | Cl | OCH3 | |
| 2.224 | CH(CH3)2 | Cl | SCH3 | |
| 2.225 | OCH2CH=CH2 | Cl | H | |
| 2.226 | Cl | CH3 | SCH3 | |
| 2.227 | Cl | CH3 | OCH2CH=CH2 | |
| 2.228 | SCH3 | Cl | Cl | |
| 2.229 | SCH3 | Cl | OCH3 | |
| 2.230 | SCH3 | Cl | SCH3 | |
| 2.231 | SCH3 | Cl | OCH2CF3 | |
| 2.232 | SCH3 | Cl | OCH2CH=CH2 | |

TABLE 3

Compounds of the formula

[Structure: 2,4-dinitro-6-trifluoromethyl-phenyl linked via NH to a pyrimidine ring bearing R$_6$, R$_7$, and =R$_5$ substituent]

| Compound | R$_5$ | R$_6$ | R$_7$ | Physical data [°C.] |
|---|---|---|---|---|
| 3.1 | H | Cl | OCH$_3$ | m.p. 75–77 |
| 3.2 | H | SCH$_3$ | SCH$_3$ | |
| 3.3 | H | OCH$_2$CF$_3$ | OCH$_2$CF$_3$ | |
| 3.4 | H | Cl | Cl | m.p. 153–154 |
| 3.5 | Cl | CH$_3$ | CH$_3$ | |
| 3.6 | SCN | CH$_3$ | CH$_3$ | |
| 3.7 | OCH$_2$CF$_3$ | CH$_3$ | CH$_3$ | |
| 3.8 | SCH$_3$ | CH$_3$ | CH$_3$ | |
| 3.9 | OC$_2$H$_5$ | CH$_3$ | CH$_3$ | |
| 3.10 | Cl | CF$_3$ | CF$_3$ | |
| 3.11 | OC$_4$H$_9$—n | CF$_3$ | CF$_3$ | |
| 3.12 | SCH$_2$CH=CH$_2$ | CF$_3$ | CF$_3$ | |
| 3.13 | F | CF$_3$ | CF$_3$ | |
| 3.14 | OCH(CH$_3$)$_2$ | CCl$_3$ | CCl$_3$ | |
| 3.15 | Cl | H | CH$_3$ | |
| 3.16 | Br | H | CH$_3$ | |
| 3.17 | OC$_2$H$_5$ | H | C$_2$H$_5$ | |
| 3.18 | SCN | H | CH$_3$ | |
| 3.19 | Cl | H | H | |
| 3.20 | OCH$_2$CH$_2$F | H | H | |
| 3.21 | O(CH$_2$)$_3$N(C$_2$H$_5$)$_2$ | H | H | |
| 3.22 | N(CH$_3$)$_2$ | H | H | |
| 3.23 | O(CH$_2$)$_2$SC$_2$H$_5$ | H | H | |
| 3.24 | Cl | Cl | Cl | |
| 3.25 | Cl | Cl | OC$_2$H$_5$ | |
| 3.26 | Cl | Cl | SC$_2$H$_5$ | |
| 3.27 | Cl | Cl | OCH$_2$CF$_3$ | |
| 3.28 | Cl | OCH$_3$ | OCH$_3$ | |
| 3.29 | Cl | OCH(CF$_3$)$_2$ | OCH(CF$_3$)$_2$ | |
| 3.30 | Cl | SCH$_3$ | SCH$_3$ | |
| 3.31 | Cl | Cl | OCH$_2$CH$_2$OCH$_3$ | |
| 3.32 | Cl | Cl | OCH$_2$CH$_2$CH$_2$Cl | |
| 3.33 | OCH$_2$CF$_3$ | OCH$_2$CF$_3$ | OCH$_2$CF$_3$ | |
| 3.34 | F | F | F | |
| 3.35 | Cl | Cl | OC$_6$H$_{13}$—n | |
| 3.36 | Cl | Cl | SC$_4$H$_9$—n | |
| 3.37 | Cl | Cl | OCH$_2$CH=CH$_2$ | |
| 3.38 | Cl | Cl | OCH$_2$C≡CH | |
| 3.39 | Cl | OCH$_2$CH=CH$_2$ | O—cyclopentyl | |
| 3.40 | Br | Br | Br | |
| 3.41 | Br | OC$_2$H$_5$ | SCH$_2$CH=CH$_2$ | |
| 3.42 | F | OC$_4$H$_9$—n | OC$_4$H$_9$—n | |
| 3.43 | Cl | OCH$_2$CH$_2$NO$_2$ | OCH$_2$CH$_2$NO$_2$ | |
| 3.44 | Cl | Cl | O(CH$_2$)$_3$OC$_3$H$_7$—n | |
| 3.45 | Cl | O(CH$_2$)$_3$N(CH$_3$)$_2$ | O(CH$_2$)$_3$N(CH$_3$)$_2$ | |
| 3.46 | OC$_6$H$_{11}$—n | OC$_6$H$_{11}$—n | OC$_6$H$_{11}$—n | |
| 3.47 | Cl | Cl | SOCH$_3$ | |
| 3.48 | Cl | Cl | SO$_2$C$_2$H$_5$ | |
| 3.49 | Cl | H | Cl | oil |
| 3.50 | F | H | F | |
| 3.51 | Cl | H | OCH$_3$ | oil |
| 3.52 | Cl | H | OC$_2$H$_5$ | |
| 3.53 | Cl | H | OCH$_2$CF$_3$ | |
| 3.54 | Cl | H | OCH$_2$CH$_2$OCH$_3$ | |
| 3.55 | Cl | H | OCH(CH$_3$)$_2$ | |
| 3.56 | Cl | H | SC$_2$H$_5$ | |
| 3.57 | Cl | H | SCH$_2$CH=CH$_2$ | |
| 3.58 | Cl | H | SO$_2$CH$_3$ | |
| 3.59 | Cl | H | SCN | |
| 3.60 | Cl | H | SC$_4$H$_9$—t | |
| 3.61 | Cl | H | O(CH$_2$)$_3$Cl | |
| 3.62 | F | H | SCH$_3$ | |
| 3.63 | F | H | OCH$_3$ | |
| 3.64 | Br | H | Br | |
| 3.65 | Br | H | SCH$_3$ | |
| 3.66 | Cl | H | CN | |
| 3.67 | SCH$_3$ | H | SCH$_3$ | |
| 3.68 | SH | H | SH | |
| 3.69 | OCH$_3$ | H | Cl | |

TABLE 3-continued

Compounds of the formula

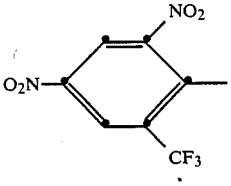

| Compound | $R_5$ | $R_6$ | $R_7$ | Physical data [°C.] |
|---|---|---|---|---|
| 3.70 | $SC_2H_5$ | H | Cl | |
| 3.71 | $OCH_2CF_3$ | H | Cl | |
| 3.72 | Cl | H | $O(CH_2)_3N(CH_3)_2$ | |
| 3.73 | Cl | H | $O(CH_2)_2OC_3H_7-n$ | |
| 3.74 | Cl | H | $OC_6H_{11}-n$ | |
| 3.75 | $OC_6H_{11}-n$ | H | Cl | |
| 3.76 | $OCH_2CH=CH_2$ | H | $SCH(CH_3)_2$ | |
| 3.77 | Cl | H | $SO_2C_2H_5$ | |
| 3.78 | Cl | $CH_3$ | Cl | |
| 3.79 | Cl | $CH_3$ | $OCH_3$ | |
| 3.80 | Cl | $CH_3$ | $SC_2H_5$ | |
| 3.81 | Cl | $CH_3$ | $OCH_2CCl_3$ | |
| 3.82 | Cl | $CH_3$ | $OCH_2C\equiv CH$ | |
| 3.83 | $SCH_3$ | $CH_3$ | $SCH_3$ | |
| 3.84 | $OCH(CH_3)_2$ | $CH_3$ | $SC_2H_5$ | |
| 3.85 | Cl | $CH_3$ | CN | |
| 3.86 | Cl | $CF_3$ | Cl | |
| 3.87 | Cl | $CF_3$ | $SCH_3$ | |
| 3.88 | Cl | $CF_3$ | $OCH_3$ | |
| 3.89 | Cl | $CCl_3$ | $SC_2H_5$ | |
| 3.90 | Cl | $CCl_3$ | $OC_4H_9-t$ | |
| 3.91 | Cl | $CCl_3$ | $OCH_2CF_3$ | |
| 3.92 | Cl | $CCl_3$ | $OCH_2CH_2OCH_3$ | |
| 3.93 | Cl | $CCl_3$ | SCN | |
| 3.94 | Cl | $CCl_3$ | $OC_6H_{13}-n$ | |
| 3.95 | $SO_2CH_3$ | $CH_3$ | $SO_2CH_3$ | |
| 3.96 | $CH_3$ | Cl | Cl | |
| 3.97 | $C_2H_5$ | F | F | |
| 3.98 | $C_6H_{11}-n$ | Cl | $OCH_3$ | |
| 3.99 | $(CH_3)_2CH$ | Cl | $OC_2H_5$ | |
| 3.100 | $CH_3$ | Cl | $SCH_3$ | |
| 3.101 | $CH_3$ | Cl | $S-C_4H_9-t$ | |
| 3.102 | $CH_3$ | Cl | $SCH_2CH=CH_2$ | |
| 3.103 | $CH_3$ | Cl | SCN | |
| 3.104 | $C_2H_5$ | Cl | O—cyclohexyl | |
| 3.105 | $C_3H_7-n$ | Cl | $O(CH_2)_3Cl$ | |
| 3.106 | $C_4H_9-n$ | Cl | $O(CH_2)_2OC_2H_5$ | |
| 3.107 | $CCl_3$ | Cl | $OCH_3$ | |
| 3.108 | $CCl_3$ | Cl | $OC_2H_5$ | |
| 3.109 | $CCl_3$ | Cl | $SC_2H_5$ | |
| 3.110 | $CCl_3$ | Cl | Cl | |
| 3.111 | $CF_3$ | Cl | Cl | |
| 3.112 | $CF_3$ | Cl | $OCH_3$ | |
| 3.113 | $CF_3$ | $SCH_3$ | $SCH_3$ | |
| 3.114 | $CF_3$ | Cl | $OCH_2CF_3$ | |
| 3.115 | $CH_3$ | $OCH_3$ | $O(CH_2)_3NH_2$ | |
| 3.116 | $CH_3$ | $SC_2H_5$ | $O(CH_2)_3Cl$ | |
| 3.117 | $CH_3$ | $SCH_2CH=CH_2$ | $S-C_4H_9-n$ | |
| 3.118 | $C_2H_5$ | $OCH_2CH_2NO_2$ | $OCH(CF_3)_2$ | |
| 3.119 | $CH_3$ | Br | Br | |
| 3.120 | $CH_3$ | Br | O—cyclopentyl | |
| 3.121 | $CH_2C_6H_5$ | Cl | Cl | |
| 3.122 | $CH_2C_6H_4Cl(4)$ | Cl | $SCH_3$ | |
| 3.123 | $CH_2C_6H_4(OCH_3)(4)$ | Cl | $OC_2H_5$ | |
| 3.124 | $CH_2C_6H_4(NO_2)(4)$ | Cl | Cl | |
| 3.125 | $C_6H_5$ | Cl | Cl | |
| 3.126 | $C_6H_5$ | Cl | $OCH_3$ | |
| 3.127 | $C_6H_5$ | Cl | $SCH_3$ | |
| 3.128 | $C_6H_5$ | Cl | $N(CH_3)_2$ | |
| 3.129 | $C_6H_4Cl(2)$ | Cl | Cl | |
| 3.130 | $C_6H_4Cl(2)$ | Cl | Cl | |
| 3.131 | $C_6H_4Cl(3)$ | Cl | $SC_2H_5$ | |
| 3.132 | $C_6H_4Cl(3)$ | Cl | $N(C_4H_9)_2$ | |
| 3.133 | $C_6H_4Cl(3)$ | Cl | $O(CH_2)_3Cl$ | |
| 3.134 | $C_6H_4Cl(4)$ | $SCH_3$ | $SCH_3$ | |
| 3.135 | $C_6H_4Cl(4)$ | $OCH_3$ | $OC_2H_5$ | |
| 3.136 | $C_6H_4Cl(4)$ | Cl | $OC_6H_{11}-n$ | |
| 3.137 | $C_6H_4CN(4)$ | Cl | $OCH_3$ | |
| 3.138 | $C_6H_4F(3)$ | Cl | Cl | |

TABLE 3-continued

Compounds of the formula

[Structure: 2,4-dinitro-6-trifluoromethyl-phenyl-NH- connected to a pyrimidine ring bearing R6, R7, and R5 substituents]

| Compound | $R_5$ | $R_6$ | $R_7$ | Physical data [°C.] |
|---|---|---|---|---|
| 3.139 | $C_6H_4F(4)$ | Cl | $SCH_3$ | |
| 3.140 | $C_6H_4(OCH_3)(2)$ | Cl | Cl | |
| 3.141 | $C_6H_4(OCH_3)(3)$ | $SC_3H_7-n$ | $C_4H_9-t$ | |
| 3.142 | $C_6H_4(NO_2)(4)$ | Cl | $OC_6H_{11}-n$ | |
| 3.143 | $C_6H_4[N(CH_3)_2](4)$ | Cl | Cl | |
| 3.144 | $C_6H_4(CF_3)(3)$ | Cl | Cl | |
| 3.145 | $C_6H_4(CF_3)(3)$ | Cl | $OCH_3$ | |
| 3.146 | $C_6H_4(CF_3)(4)$ | Cl | $SCH_3$ | |
| 3.147 | $C_6H_3Cl_2(2,4)$ | Cl | Cl | |
| 3.148 | $C_6H_3(NO_2)_2(3,5)$ | Cl | $OC_2H_5$ | |
| 3.149 | $C_6H_3Cl_2(2,4)$ | Cl | $OC_2H_5$ | |
| 3.150 | $C_6H_3(NO_2)(3,5)$ | Cl | Cl | |
| 3.151 | $C_6H_4(CH_3)(4)$ | Cl | Cl | |
| 3.152 | $C_6H_4(CH_3)(4)$ | Cl | $SCH_2CH=CH_2$ | |
| 3.153 | $C_6H_4(C_4H_9-t)(4)$ | Cl | Cl | |
| 3.154 | $SCH_3$ | H | $OC_3H_7-n$ | |
| 3.155 | $SCH_3$ | H | $O(CH_2)_2OCH_3$ | |
| 3.156 | $SCH_3$ | H | $O(CH_2)_3N(C_2H_5)_2$ | |
| 3.157 | $N(CH_3)_2$ | H | Cl | |
| 3.158 | $N(C_2H_5)_2$ | H | $OC_2H_5$ | |
| 3.159 | $N(CH_3)_2$ | H | $O(CH_2)_3Cl$ | |
| 3.160 | $C_6H_5$ | H | Cl | |
| 3.161 | $C_6H_5$ | H | $SC_2H_5$ | |
| 3.162 | $CH_3$ | Cl | $CH_3$ | |
| 3.163 | $CH_2C_6H_5$ | $OCH_3$ | $CH_3$ | |
| 3.164 | $C_6H_5$ | Cl | $CH_3$ | |
| 3.165 | $SCH_3$ | $OCH_2CF_3$ | $CF_3$ | |
| 3.166 | $CH_3$ | $CH_3$ | $CH_3$ | |
| 3.167 | $C_5H_{11}-n$ | $CH_3$ | $CH_3$ | |
| 3.168 | $C_6H_4(4)$ | $CF_3$ | $CF_3$ | |
| 3.169 | $C_6H_4CN(3)$ | $CF_3$ | $CF_3$ | |
| 3.170 | $N(CH_3)_2$ | $CH_3$ | $CH_3$ | |
| 3.171 | $SCH_3$ | H | $CH_3$ | |
| 3.172 | $C_2H_5$ | H | $CH_3$ | |
| 3.173 | $C_6H_4Cl(2)$ | H | $CH_3$ | |
| 3.174 | $CH_3$ | H | H | |
| 3.175 | $SCH_3$ | H | H | |
| 3.176 | $C_6H_4(CF_3)(4)$ | H | H | |
| 3.177 | $C_6H_4(OCH_3)(3)$ | H | H | |
| 3.178 | H | Cl | $OC_2H_5$ | |
| 3.179 | H | Cl | $OCH(CH_3)C_2H_5$ | |
| 3.180 | H | Cl | O—cyclohexyl | |
| 3.181 | H | Cl | $OCH_2CF_3$ | |
| 3.182 | H | Cl | $OCH_2CH=CH_2$ | m.p. 87-88 |
| 3.183 | H | Cl | $OCH_2CH_2OCH_3$ | |
| 3.184 | H | Cl | $SCH_3$ | |
| 3.185 | H | Cl | $SCH_3$ | |
| 3.186 | H | Cl | $SCH(CH_3)_2$ | |
| 3.187 | H | Cl | SCN | |
| 3.188 | H | SCN | SCN | |
| 3.189 | H | Cl | $S(O)CH_3$ | |
| 3.190 | H | Cl | $SO_2CH_3$ | |
| 3.191 | H | SH | SH | |
| 3.192 | H | F | F | |
| 3.193 | H | $OCH(CF_3)_2$ | $OCH(CF_3)_2$ | |
| 3.194 | H | Cl | $O(CH_2)_3Cl$ | |
| 3.195 | H | $OCH_2CH_2NO_2$ | $O(CH_2)_3OC_2H_5$ | |
| 3.196 | H | Cl | $O(CH_2)_2N(C_4H_9-n)_2$ | |
| 3.197 | H | Cl | $OCH_2CH_2NO_2$ | |
| 3.198 | H | $OCH_3$ | $O(CH_2)_3N(CH_3)_2$ | |
| 3.199 | H | $SC_2H_5$ | $OCH_3$ | |
| 3.200 | H | $SCH_2CH=CH_2$ | $N(C_4H_9-n)_2$ | |
| 3.201 | H | $N(CH_3)_2$ | $N(C_2H_5)_2$ | |
| 3.202 | H | F | $SCH_3$ | |
| 3.203 | H | $S-C_4H_9-t$ | $O(CH_2)_2OC_4H_9-n$ | |
| 3.204 | H | Cl | $OCH_2CH_2CN$ | |
| 3.205 | H | $OCH_3$ | $OCH_3$ | m.p. 172-174 |
| 3.206 | $CH_3$ | Cl | $OCH_3$ | m.p. 110-111 |
| 3.207 | $C_2H_5$ | Cl | $OCH_3$ | m.p. 98-99 |

TABLE 3-continued

Compounds of the formula

[Structure: 2,4-dinitro-6-trifluoromethyl-phenyl group with NH linkage to pyrimidine ring bearing R6, R7, R5 substituents]

| Compound | R5 | R6 | R7 | Physical data [°C.] |
|---|---|---|---|---|
| 3.208 | C2H5 | Cl | Cl | |
| 3.209 | C2H5 | Cl | SCH3 | |
| 3.210 | Cl | H | OCH2CH2SC2H5 | |
| 3.211 | Cl | H | OCH2C≡CH | |
| 3.212 | Cl | H | OCH2CH=CH2 | |
| 3.213 | H | Cl | OCH2C≡CH | |
| 3.214 | CH3 | Cl | OCH2CF3 | |
| 3.215 | CH3 | Cl | OCH2CH=CH2 | |
| 3.216 | CH3 | Cl | OCH2C≡CH | |
| 3.217 | CH(CH3)2 | Cl | Cl | |
| 3.218 | CH(CH3)2 | Cl | OCH3 | |
| 3.219 | CH(CH3)2 | Cl | SCH3 | |
| 3.220 | OCH2CH=CH2 | Cl | H | |
| 3.221 | Cl | CH3 | SCH3 | |
| 3.222 | Cl | CH3 | OCH2CH=CH2 | |
| 3.223 | SCH3 | Cl | Cl | |
| 3.224 | SCH3 | Cl | OCH3 | |
| 3.225 | SCH3 | Cl | SCH3 | |
| 3.226 | SCH3 | Cl | OCH2CF3 | |
| 3.227 | SCH3 | Cl | OCH2CH=CH2 | |

TABLE 4

Compounds of the formula

[Structure: 3-chloro-2,6-dinitro-4-trifluoromethyl-phenyl group with N(R4) linkage to pyrimidine ring bearing R6, R7, R5 substituents]

| Compound | R5 | R6 | R7 | R4 | Physical data [°C.] |
|---|---|---|---|---|---|
| 4.1 | H | Cl | OCH3 | C(O)CH3 | m.p. 181–182 |
| 4.2 | H | SCH3 | SCH3 | C(O)CH3 | |
| 4.3 | H | OCH2CF3 | OCH2CF3 | C(O)C2H5 | |
| 4.4 | H | Cl | Cl | C(O)CH2Cl | |
| 4.5 | Cl | CH3 | CH3 | C(O)CH3 | |
| 4.6 | SCN | CH3 | CH3 | C(O)CH2OCH3 | |
| 4.7 | OCH2CF3 | CH3 | CH3 | C(O)CH3 | |
| 4.8 | SCH3 | CH3 | CH3 | C(O)C2H5 | |
| 4.9 | OC2H5 | CH3 | CH3 | C(O)CH3 | |
| 4.10 | Cl | CF3 | CF3 | C(O)CH3 | |
| 4.11 | OC4H9—n | CF3 | CF3 | C(O)CH3 | |
| 4.12 | SCH2CH=CH2 | CF3 | CF3 | C(O)CH2OC2H5 | |
| 4.13 | F | CF3 | CF3 | C(O)CH2OCH3 | |
| 4.14 | OCH(CH3)2 | CCl3 | CCl3 | C(O)CH2OCH3 | |
| 4.15 | Cl | H | CH3 | C(O)CH3 | |
| 4.16 | Br | H | CH3 | C(O)CH2Cl | |
| 4.17 | OC2H5 | H | C2H5 | C(O)CH2Cl | |
| 4.18 | SCN | H | CH3 | C(O)CH3 | |
| 4.19 | Cl | H | H | C(O)CH3 | |
| 4.20 | OCH2CH2F | H | H | C(O)CH3 | |
| 4.21 | O(CH2)3N(C2H5)2 | H | H | C(O)CH3 | |
| 4.22 | N(CH3)2 | H | H | C(O)CH3 | |
| 4.23 | O(CH2)2SC2H5 | H | H | C(O)CH3 | |
| 4.24 | H | Cl | OC2H5 | C(O)CH3 | m.p. 108–109 |

TABLE 5

Compounds of the formula

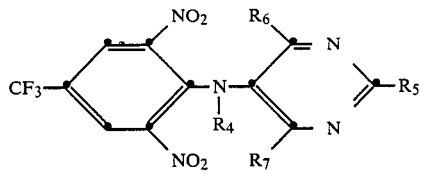

| Compound | R5 | R6 | R7 | R4 |
|---|---|---|---|---|
| 5.1 | H | Cl | $OCH_3$ | $C(O)CH_3$ |
| 5.2 | H | $SCH_3$ | $SCH_3$ | $C(O)CH_3$ |
| 5.3 | H | $OCH_2CF_3$ | $OCH_2CF_3$ | $C(O)C_2H_5$ |
| 5.4 | H | Cl | Cl | $C(O)CH_2Cl$ |
| 5.5 | Cl | $CH_3$ | $CH_3$ | $C(O)CH_3$ |
| 5.6 | SCN | $CH_3$ | $CH_3$ | $C(O)CH_2OCH_3$ |
| 5.7 | $OCH_2CF_3$ | $CH_3$ | $CH_3$ | $C(O)CH_3$ |
| 5.8 | $SCH_3$ | $CH_3$ | $CH_3$ | $C(O)C_2H_5$ |
| 5.9 | $OC_2H_5$ | $CH_3$ | $CH_3$ | $C(O)CH_3$ |
| 5.10 | Cl | $CF_3$ | $CF_3$ | $C(O)CH_3$ |
| 5.11 | $OC_4H_9-n$ | $CF_3$ | $CF_3$ | $C(O)CH_3$ |
| 5.12 | $SCH_2CH=CH_2$ | $CF_3$ | $CF_3$ | $C(O)CH_2OC_2H_5$ |
| 5.13 | F | $CF_3$ | $CF_3$ | $C(O)CH_2OCH_3$ |
| 5.14 | $OCH(CH_3)_2$ | $CCl_3$ | $CCl_3$ | $C(O)CH_2OCH_3$ |
| 5.15 | Cl | H | $CH_3$ | $C(O)CH_3$ |
| 5.16 | Br | H | $CH_3$ | $C(O)CH_2Cl$ |
| 5.17 | $OC_2H_5$ | H | $C_2H_5$ | $C(O)CH_2Cl$ |
| 5.18 | SCN | H | $CH_3$ | $C(O)CH_3$ |
| 5.19 | Cl | H | H | $C(O)CH_3$ |
| 5.20 | $OCH_2CH_2F$ | H | H | $C(O)CH_3$ |
| 5.21 | $O(CH_2)_3N(C_2H_5)_2$ | H | H | $C(O)CH_3$ |
| 5.22 | $N(CH_3)_2$ | H | H | $C(O)CH_3$ |
| 5.23 | $O(CH_2)_2SC_2H_5$ | H | H | $C(O)CH_3$ |

TABLE 6

Compounds of the formula

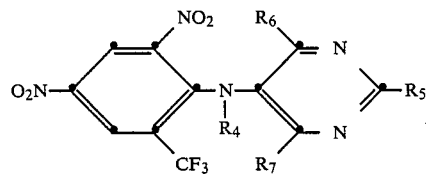

| Compound | R5 | R6 | R7 | R4 | Physical data [°C.] |
|---|---|---|---|---|---|
| 6.1 | H | Cl | $OCH_3$ | $C(O)CH_3$ | m.p. 167–169 |
| 6.2 | H | $SCH_3$ | $SCH_3$ | $C(O)CH_3$ | |
| 6.3 | H | $OCH_2CF_3$ | $OCH_2CF_3$ | $C(O)C_2H_5$ | |
| 6.4 | H | Cl | Cl | $C(O)CH_2Cl$ | |
| 6.5 | Cl | $CH_3$ | $CH_3$ | $C(O)CH_3$ | |
| 6.6 | SCN | $CH_3$ | $CH_3$ | $C(O)CH_2OCH_3$ | |
| 6.7 | $OCH_2CF_3$ | $CH_3$ | $CH_3$ | $C(O)CH_3$ | |
| 6.8 | $SCH_3$ | $CH_3$ | $CH_3$ | $C(O)C_2H_5$ | |
| 6.9 | $OC_2H_5$ | $CH_3$ | $CH_3$ | $C(O)CH_3$ | |
| 6.10 | Cl | $CF_3$ | $CF_3$ | $C(O)CH_3$ | |
| 6.11 | $OC_4H_9-n$ | $CF_3$ | $CF_3$ | $C(O)CH_3$ | |
| 6.12 | $SCH_2CH=CH_2$ | $CF_3$ | $CF_3$ | $C(O)CH_2OC_2H_5$ | |
| 6.13 | F | $CF_3$ | $CF_3$ | $C(O)CH_2OCH_3$ | |
| 6.14 | $OCH(CH_3)_2$ | $CCl_3$ | $CCl_3$ | $C(O)CH_2OCH_3$ | |
| 6.15 | Cl | H | $CH_3$ | $C(O)CH_3$ | |
| 6.16 | Br | H | $CH_3$ | $C(O)CH_2Cl$ | |
| 6.17 | $OC_2H_5$ | H | $C_2H_5$ | $C(O)CH_2Cl$ | |
| 6.18 | SCN | H | $CH_3$ | $C(O)CH_3$ | |
| 6.19 | Cl | H | H | $C(O)CH_3$ | |
| 6.20 | $OCH_2CH_2F$ | H | H | $C(O)CH_3$ | |
| 6.21 | $O(CH_2)_3N(C_2H_5)_2$ | H | H | $C(O)CH_3$ | |
| 6.22 | $N(CH_3)_2$ | H | H | $C(O)CH_3$ | |
| 6.23 | $O(CH_2)_2SC_2H_5$ | H | H | $C(O)CH_3$ | |

TABLE 7

Compounds of the formula $$\text{R}_2\text{-C}_6\text{H}_2(\text{NO}_2)_2\text{-NH-C(R}_6)\text{=N-...=N-R}_7, \text{=CR}_5$$

| Compound | R5 | R6 | R7 | R2 | m.p. [°C.] |
|---|---|---|---|---|---|
| 7.1 | H | Cl | Cl | NO2 | 161–163 |
| 7.2 | Cl | Cl | H | NO2 | 181–183 |
| 7.3 | H | Cl | OCH2CF3 | NO2 | |
| 7.4 | H | SCH3 | Cl | NO2 | |
| 7.5 | Cl | H | H | NO2 | |
| 7.6 | Cl | H | OCH3 | NO2 | |
| 7.7 | Cl | SCH3 | H | NO2 | |
| 7.8 | CH3 | Cl | Cl | NO2 | |
| 7.9 | (CH3)2CH | OCH2C≡CH | Cl | NO2 | |
| 7.10 | CH3 | OCH2CH=CH2 | Cl | NO2 | |
| 7.11 | CH3 | Cl | OCH(CH3)2 | NO2 | |
| 7.12 | Cl | Cl | CH3 | NO2 | |
| 7.13 | Cl | OCH3 | CH3 | NO2 | |
| 7.14 | SCH3 | Cl | Cl | NO2 | |
| 7.15 | Cl | Cl | Cl | NO2 | |
| 7.16 | F | F | H | NO2 | |
| 7.17 | C2H5 | Cl | Cl | NO2 | 130–131 |

TABLE 8

Compounds of the formula $$\text{CF}_2\text{-C}_6\text{H}_3(\text{NO}_2)\text{-NH-C(R}_6)\text{=N-...=N-R}_7, \text{=CR}_5$$

| Compound | R5 | R6 | R7 | m.p. [°C.] |
|---|---|---|---|---|
| 8.1 | H | Cl | Cl | 119–121 |
| 8.2 | H | Cl | OCH3 | 117–118 |
| 8.3 | Cl | Cl | H | 98 |
| 8.4 | Cl | Cl | CH3 | |
| 8.5 | CH3 | OCH3 | Cl | |
| 8.6 | H | OC2H5 | Cl | |
| 8.7 | H | Cl | SCH3 | |
| 8.8 | H | Cl | OCH2C≡CH | |
| 8.9 | H | Cl | OCH2CH=CH2 | oil |
| 8.10 | C2H5 | SCH3 | Cl | |
| 8.11 | CH(CH3)2 | OC4H9 | Cl | |
| 8.12 | CH3S | Cl | Cl | |
| 8.13 | Cl | Cl | Cl | |
| 8.14 | H | H | H | |
| 8.15 | H | Cl | OCH2CF3 | |
| 8.16 | Cl | Cl | OCH(CH3)2 | |
| 8.17 | CH3S | OCH3 | Cl | |
| 8.18 | CH3 | Cl | SCH3 | |
| 8.19 | CH3 | OCH2C≡CH | Cl | |
| 8.20 | H | Br | OCH3 | |
| 8.21 | H | F | F | |
| 8.22 | CH(CH3)2 | SCH2CH=CH2 | Cl | |
| 8.23 | CH(CH3)2 | Cl | Cl | |
| 8.24 | C2H5 | Cl | OCH3 | |
| 8.25 | C2H5 | Cl | OCH2CH=CH2 | |
| 8.26 | CH3 | OCH(CH3)2 | OCH3 | |
| 8.27 | CH3 | SCH3 | OC2H5 | |
| 8.28 | H | Cl | OC(CH3)3 | 111 |
| 8.29 | Cl | H | OCH3 | |
| 8.30 | Cl | H | OCH2 | |
| 8.31 | CH(CH3)2 | Cl | OCH3 | |

TABLE 8-continued

Compounds of the formula $$\text{CF}_2\text{-C}_6\text{H}_3(\text{NO}_2)\text{-NH-C(R}_6)\text{=N-...=N-R}_7, \text{=CR}_5$$

| Compound | R5 | R6 | R7 | m.p. [°C.] |
|---|---|---|---|---|
| 8.32 | CH(CH3)2 | Cl | SCH3 | |
| 8.33 | SCH3 | Cl | OCH2CF3 | |
| 8.34 | SCH3 | Cl | OCH2CH=CH2 | |
| 8.35 | SCH3 | Cl | OCH2C≡CH | |

TABLE 9

Compounds of the formula $$\text{Cl, O}_2\text{N-C}_6\text{H}(\text{NO}_2)(\text{CF}_3)\text{-NH-C(R}_6)\text{=N-...=N-R}_7, \text{=CR}_5$$

| Compound | R5 | R6 | R7 | m.p. [°C.] |
|---|---|---|---|---|
| 9.1 | H | Cl | SCH3 | 172–176 |
| 9.2 | H | OCH3 | H | 108–110 |
| 9.3 | H | OCH3 | OCH3 | 196–199 |
| 9.4 | CH3 | OC2H5 | H | 124–126 |
| 9.5 | Cl | H | OCH3 | 143–146 |

FORMULATION EXAMPLES

Formulation Examples for liquid active ingredients of the formula I (throughout, percentages are by weight)

| F1. Emulsifiable concentrates | (a) | (b) | (c) |
|---|---|---|---|
| a compound of tables 1 to 9 | 25% | 40% | 50% |
| calcium dodecylbenzenesulfonate | 5% | 8% | 6% |
| castor oil polyethylene glycol ether (36 moles of ethylene oxide) | 5% | — | — |
| tributylphenol polyethylene glycol ether (30 moles of ethylene oxide) | — | 12% | 4% |
| cyclohexanone | — | 15% | 20% |
| xylene mixture | 65% | 25% | 20% |

Emulsions of any required concentration can be produced from such concentrates by dilution with water.

| F2. Solutions | (a) | (b) | (c) | (d) |
|---|---|---|---|---|
| a compound of tables 1 to 9 | 80% | 10% | 5% | 95% |
| ethylene glycol monomethyl ether | 20% | — | — | — |
| polyethylene glycol 400 | — | 70% | — | — |
| N—methyl-2-pyrrolidone | — | 20% | — | — |
| epoxidised coconut oil | — | — | 1% | 5% |
| petroleum distillate (boiling range 160-190°) | — | — | 94% | — |

These solutions are suitable for application in the form of microdrops.

| F3. Granulates | (a) | (b) |
|---|---|---|
| a compound of tables 1 to 9 | 5% | 10% |
| kaolin | 94% | — |
| highly dispersed silicic acid | 1% | — |

-continued

| F3. Granulates | (a) | (b) |
|---|---|---|
| attapulgite | — | 90% |

The active ingredient is dissolved in methylene chloride, the solution is sprayed onto the carrier, and the solvent is subsequently evaporated off in vacuo.

| F4. Dusts | (a) | (b) |
|---|---|---|
| a compound of tables 1 to 9 | 2% | 5% |
| highly dispersed silicic acid | 1% | 5% |
| talcum | 97% | — |
| kaolin | — | 90% |

Ready-for-use dusts are obtained by intimately mixing the carriers with the acitve ingredient.

Formulation examples for solid active ingredients of the formula I (throughout, percentages are by weight)

| F5. Wettable powders | (a) | (b) | (c) |
|---|---|---|---|
| a compound of tables 1 to 9 | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| octylphenol polyethylene glycol ether (7–8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixtures is thoroughly ground in a suitable mill, affording wettable powders which can be diluted with water to give suspensions of the desired concentration.

| F6. Emulsifiable concentrate | |
|---|---|
| a compound of tables 1 to 9 | 10% |
| octylphenol polyethylene glycol ether (4–5 moles of ethylene oxide) | 3% |
| calcium dodecylbenzenesulfonate | 3% |
| castor oil polyglycol ether (36 moles of ethylene oxide) | 4% |
| cyclohexanone | 30% |
| xylene mixture | 50% |

Emulsions of any required concentration can be obtained from this concentrate by dilution with water.

| F7. Dusts | (a) | (b) |
|---|---|---|
| a compound of tables 1 to 9 | 5% | 8% |
| talcum | 95% | — |
| kaolin | — | 92% |

Ready-for-use dusts are obtained by mixing the active ingredient with the carriers, and grinding the mixture in a suitable mill.

| F8. Extruder granulate | |
|---|---|
| a compound of tables 1 to 9 | 10% |
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and then dried in a strem of air.

| F9. Coated granulate | |
|---|---|
| a compound of tables 1 to 9 | 3% |
| polyethylene glycol 200 | 3% |
| kaolin | 94% |

The finely ground active ingredient is uniformly applied, in a mixer, to the kaolin moistened with polyethylene glycol. Non-dusty coated granulates are obtained in this manner.

| F10. Suspension concentrate | |
|---|---|
| a compound of tables 1 to 9 | 40% |
| ethylene glycol | 10% |
| nonylphenol polyethylene glycol (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the aduvants, giving a suspension concentrate from which suspensions of any desired concentration can be obtained by dilution with water.

BIOLOGICAL EXAMPLES

Example B1:

Action against Puccinia graminis on wheat (a) Residual-protective action

Wheat plants were treated 6 days after sowing with a spray mixture prepared from a wettable powder formulation of the active ingredient (0.02%). After 24 hours the treated plants were infected with a uredospore suspension of the fungus. The infected plants were incubated for 48 hours at 95–100% relative humidity and about 20° C. and then stood in a greenhouse at about 22° C. Evaluation of rust pustule development was made 12 days after infection.

(b) Systemic action

Wheat plants were treated 5 days after sowing with a spray mixture prepared from a wettable powder formulation of the active ingredient (0.006% based on the volume of the soil). After 48 hours the treated plants were infected with a uredospore suspension of the fungus. The plants were then incubated for 48 hours at 95–100% relative humidity and about 20° C. and then stood in a greenhouse at about 22° C. Evaluation or rust pustule development was made 12 days after infection.

Compounds of the tables were very effective against Puccinia fungi. Puccinia attack on untreated and infected control plants was 100%. Compounds 1.1 to 1.4, 1.19, 1.49, 1.51, 1.57, 1.78, 1.96, 1.111, 1.125, 1.151, 1.178, 1.184, 1.205, 1.207, 1.210, 1.211, 1.213, 1.214, 1.216, 1.218, 1.220, 2.1, 2.4, 2.49, 2.51, 2.96, 2.207, 2.208, 2.210, 2.211, 2.212, 3.1, 3.4, 3.49, 3.51, 3.206, 4.1, 4.24, 6.1, 7.1, 7.2, 8.1, 8.2, 8.3, 8.28, 9.1 and others inhibited Puccinia attack to 0 to 5%.

Example B2:

Action against *Cercospora arachidicola* in groundnut plants

Residual protective action

Groundnut plants 10-15 cm in height were sprayed with a spray mixture (0.006%) prepared from a wettable powder formulation of the test compound, and infected 48 hours later with a conidia suspension of the fungus. The infected plants were incubated for 72 hours at about 21° C. and high humidity and then stood in a greenhouse until the typical leaf specks occur. Evaluation of the fungicidal action was made 12 days after infection and was based on the number and size of the specks.

Compared with untreated and infected controls (number and size of the specks=100%), Cersospora attack in groundnut plants treated with compounds of the tables was substantially reduced. In the above tests, compounds 1.1 to 1.4, 1.19, 1.49, 1.78, 1.96, 1.111, 1.125, 1.126, 1.151, 1.178, 1.184, 1.205, 1.206, 1.207, 1.213, 1.216, 1.218, 1.220, 2.1, 2.4, 2.49, 2.51, 2.96, 2.211, 2.212, 2.1, 2.4, 3.49, 3.51, 3.207, 4.1, 4.24, 6.1, 7.1, 7.2, 8.1, 8.3, 8.28 and 9.1 inhibited the occurence of specks almost completely (0-10%).

Example B3:

Action against *Erysiphe graminis* on barley (a) Residual protective action

Barley plants about 8 cm in height were sprayed with a spray mixture (0.002%) prepared from the active ingredient formulated as a wettable powder. The treated plants were dusted with conidia of the fungus after 3-4 hours. The infected barley plants were then stood in a greenhouse at about 22° C. The extent of the infestation was evaluated after 10 days.

(b) Systemic action

Barley plants about 8 cm in height were treated with a spray mixture (0.006%), based on the colume of the soil) prepared from the test compound formulated as wettable powder. Care was taken that the spray mixture did not come in contact with the growing parts of the plants. The treated plants were infected 48 hours later with a conidia suspension of the fungus. The infected barley plants were then stood in a greenhouse at about 22° C. and evaluation of infestation was made after 10 days.

Compounds of formula I were very effective gainst Erysiphe fungi. Erysiphe attack was 100% on untreated and infected control plants. Individual compounds of the tables, inhibited fungus attack on barley to less than 30%.

Example B4:

Residual-protective action against *Venturia inaequalis* on apple shoots

Apple cuttings with 10-20 cm long fresh shoots were sprayed with a spray mixture (0.006%) prepared from a wettable powder formulation of the test compound. The plants were infected 24 hours later with a conidia suspension of the fungus. The plants were then incubated for 5 days at 90-100% relative humidity and stood in a greenhouse for a further 10 days at 20°-24° C. Scab infestation was evaluated 15 days after infection. Compounds of the tables, e.g. compounds 1.1, 1.51, 1.126, 1.127, 1.178, 1.184, 1.205, 1.206, 1.210, 1.211, 1.215, 1.217, 1.218, 2.4, 2.51, 2.96, 2.207, 2.208, 2.210, 2.211, 3.1, 3.4, 3.205, 3.206, 4.1, 4.24, 6.1, 7.17, 8.1 and 8.2, inhibited attack to less than 25%. On the other hand, attack on untreated and infected control shoots was 100%.

Example B5:

Action against *Botrytis cinerea* on beans

Residual protective action

Bean plants about 10 cm in height were sprayed with a spray mixture (0.02% concentration) prepared from a wettable powder formulation of the test compound. After 48 hours, the treated plants were infected with a conidia suspension of the fungus. The infected plants were incubated for 3 days at 95-100% relative humidity and 21° C., and evaluation of fungus attack was then made. Numerous compounds of the tables very strongly inhibited the fungus infection. At a concentration of 0.02%, compounds 1.1 to 1.4, 1.49, 1.51, 1.57, 1.196, 1.184, 1.210, 1.211 and 2.4, were fully effective (0 to 8% attack). Botrytis attack on untreated and infected bean plants was 100%.

Example B6:

Action against *Phytophthora infestans* on tomato plants (a) Residual protective action After a cultivation period of 3 weeks, tomato plants were sprayed with a spray mixture (0.06%) prepared from a wettable powder formulation of the test compound. After 24 hours the treated plants were infected with a sporangia suspension of the fungus. Evaluation of fungus attack was made after the plants had been incubated for 5 days at 90-100% relative humidity and 20° C.

(b) Systemic action

A spray mixture (0.06%, based on the volume of the soil) prepared from a wettable powder formulation of the text compound was poured on tomato plants after a cultivation period of 3 weeks. Care was taken that the spray mixture did not come in contact with the growing parts of the plants. After 48 hours the plants were infected with a sporangia suspension of the fungus. Evaluation of fungus attack was made after the plants had been incubated for 5 days at 90-100% relative humidity and 20° C.

In the above tests, compounds 1.1 to 1.4, 1.19, 1.49, 1.51, 1.57, 1.78, 1.96, 1.111, 1.125, 1.151, 1.178, 1.184, 1.205, 1.207, 1.210, 1.211, 1.213, 1.214, 1.216, 1.218, 1.220, 2.1, 2.4, 2.49, 2.51, 2.96, 2.207, 2.208, 2.210, 2.211, 2.212, 3.1, 3.4, 3.49, 3.51, 3.206, 4.1, 4.24, 6.1, 7.1, 7.2, 8.1, 8.2, 8.3, 8.28, 9.1 , and others had a very good systemic action. These compounds inhibited fungus attack almost completely (0 to 5% attack) as against 100% attack on untreated control plants.

Example B7:

Action against *Plasmapora viticola* on vines (a) Residual protective action

Vine cuttings in the 4-5 leaf stage were sprayed with a spray mixture (0.06%) prepared from a wettable powder formulation of the test compound. After 24 hours the treated plants were infected with a sporangia suspension of the fungus. Fungus attack was evaluated after incubation for 6 days at 95-100% relative humidity and 20° C.

(b) Residual curative action

Vine cuttings in the 4-5 leaf stage were infected with a sporangia suspension of the fungus. After incubation for 24 hours in a humid chamber at 95-100% relative humidity and 20° C., the infected plants were dried and sprayed with a spray mixture (0.06%) prepared from a wettable powder formulation of the test compound. After the spray coating had dried, the treated plants were returned to the humid chamber. Evaluation of fungus attack was made 6 days after infection.

Compounds of Tables 1 to 8 exhibited a very good fungicidal action against Plasmopara viticola on vines. For example, compounds 1.1, 1.2, 1.3 and 1.4 inhibited fungus attack completely (0 to 5%).

Example B8:

Action against Piricularia on rice plants

Residual protective action

After a cultivation period of 2 weeks, rice plants were sprayed with a spray mixture (0.02%) prepared from a wettable powder formulation of the test compound. After 48 hours the treated plants were infected with a conidia suspension of the fungus. Evaluation of fungus attack was made after incubation for 5 days at 95-100% relative humidity and 24° C.

Compared with 100% attack on untreated controls, fungus attack was less than 10% on rice plants which had been treated with a spray mixture containing one of compounds 1.1, 1.2, 1.3, 1.4, 1.51, 1.96, 1.205, 2.4, 3.51, and 8.1.

What is claimed is:

1. A compound of the formula

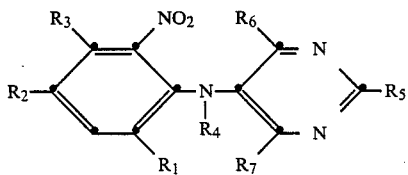

wherein
$R_1$ and $R_2$ are each independently $NO_2$ or $CF_3$, or one of $R_1$ and $R_2$ is hydrogen,
$R_3$ is hydrogen or halogen,
$R_4$ is hydrogen or the —C(O)R' group, in which R' is $C_1$–$C_4$alkyl which is unsubstituted or substituted by one halogen, $C_1$–$C_3$alkoxy or $C_1$–$C_3$alkylthio,
$R_5$, $R_6$ and $R_7$ are each independently hydrogen, halogen, nitro, cyano, thiocyano, mercapto, $C_1$–$C_6$alkyl, $C_1$–$C_6$haloalkyl, $C_1$–$C_6$alkoxy, $C_1$–$C_6$alkoxy which is substituted by one halogen, nitro, cyano, $C_1$–$C_3$alkoxy, $C_1$–$C_3$alkylthio and/or $N(C_1$–$C_4$alkyl)$_2$; or are $C_3$–$C_6$cycloalkoxy, $C_3$–$C_6$alkenyloxy, $C_3$–$C_6$alkynyloxy, $C_1$–$C_6$alkylthio, $C_3$–$C_6$alkenylthio, $C_1$–$C_6$alkylsulfonyl, $C_1$–$C_6$alkylsulfoxyl, $C_3$–$C_6$alkenyl, $C_3$–$C_6$haloalkenyl, $C_3$–$C_6$alkynyl, $C_3$–$C_6$haloalkynyl or the $N(C_1$–$C_4$alkyl)$_2$ group, and $R_5$ may additionally be a phenyl or benzyl group which are both unsubstituted or substituted by one to three identical or different members selected from halogen, nitro, cyano, $C_1$–$C_4$alkyl, $C_1$–$C_3$haloalkyl, N-($C_1$–$C_3$alkyl)$_2$, and/or $C_1$–$C_3$alkoxy.

2. A compound of claim 1, wherein $R_1$ is $NO_2$ or $CF_3$, $R_2$ is $NO_2$ or $CF_3$, $R_3$ is hydrogen or halogen, $R_4$ is hydrogen or the —C(O)R' group, in which R' is $C_1$–$C_4$alkyl which is unsubstituted or substituted by halogen, $C_1$–$C_3$alkoxy or $C_1$–$C_3$alkylthio; $R_5$, $R_6$ and $R_7$, are each independently hydrogen, halogen, nitro, cyano, thiocyano, mercapto, $C_1$–$C_6$alkyl, $C_1$–$C_6$haloalkyl, $C_1$–$C_6$alkoxy, $C_1$–$C_6$alkoxy which is substituted by halogen, nitro, cyano, $C_1$–$C_3$alkoxy, $C_1$–$C_3$alkylthio and/or N—($C_1$–$C_4$alkyl)$_2$; or are $C_3$–$C_6$cycloalkoxy, $C_3$–$C_6$alkenyloxy, $C_3$–$C_6$alkynyloxy, $C_1$–$C_6$alkylthio, $C_3$–$C_6$alkenylthio, $C_1$–$C_6$alkylsulfonyl, $C_1$–$C_6$alkylsulfoxyl, or the $N(C_1$–$C_4$alkyl)$_2$ group, and $R_5$ may additionally be a phenyl or benzyl group which is unsubstituted or substituted by one to three identical or different members selected from halogen, nitro, cyano, $C_1$–$C_4$alkyl, $C_1$–$C_3$haloalkyl, $N(C_1$–$C_3$alkyl)$_2$, and/or $C_1$–$C_3$alkoxy.

3. A compound of claim 2, wherein $R_1$ is nitro, $R_2$ is trifluoromethyl, $R_3$ is chlorine, $R_4$ is hydrogen or the —C(O)—R' group, in which R' is $C_1$–$C_4$alkyl which is unsubstituted or substituted by halogen, $C_1$–$C_3$alkoxy or $C_1$–$C_3$alkylthio; $R_5$ is hydrogen, halogen, cyano, thiocyano, $C_1$–$C_6$alkyl, $C_1$–$C_3$haloalkyl, $C_1$–$C_6$alkoxy, $C_1$–$C_3$haloalkoxy, $C_1$–$C_3$alkylthio-($C_1$–$C_3$alkoxy), $C_1$–$C_3$alkylthio, $C_1$–$C_3$alkoxy which is substituted by $N(C_1$–$C_2$alkyl)$_2$, or is $C_3$–$C_4$alkenyloxy, $C_3$–$C_4$alkenylthio, $C_1$–$C_3$alkylsulfonyl, $C_1$–$C_3$alkylsulfoxyl, $N(C_1$–$C_3$alkyl)$_2$, or a phenyl or benzyl group which are both unsubstituted or substituted by 1 to 3 identical or different members selected from fluorine, chlorine, bromine, nitro, cyano, methoxy, $C_1$–$C_4$alkyl, dimethylamino or $CF_3$; and $R_6$ and $R_7$ each independently of the other are hydrogen, halogen, cyano, thiocyano, $C_1$–$C_6$alkyl, $C_1$–$C_3$haloalkyl, $C_1$–$C_6$alkoxy, $C_1$–$C_3$alkoxy which is substituted by halogen, nitro, $C_1$–$C_3$alkoxy, $C_1$–$C_3$alkylthio or $N(C_1$–$C_4$alkyl)$_2$, or are $C_1$–$C_4$alkylthio, $C_1$–$C_3$alkylsulfonyl, $C_1$–$C_3$alkylsulfoxyl, $C_3$–$C_4$alkenyloxy, $C_3$–$C_4$alkenylthio, $C_3$–$C_4$alkynyloxy, $C_3$–$C_4$alkynylthio or $N(C_1$–$C_3$alkyl)$_2$.

4. A compound of claim 3, wherein $R_4$ is hydrogen and the other substitutents are as defined in claim 3.

5. A compound of to claim 2, wherein $R_1$ is nitro, $R_2$ is trifluoromethyl, $R_3$ is hydrogen, $R_4$ is hydrogen or the —C(O)R' group, in which R' is $C_1$–$C_4$alkyl which is unsubstituted or substituted by halogen, $C_1$–$C_3$alkoxy or $C_1$–$C_3$alkylthio; $R_5$ is hydrogen, halogen, cyano, thiocyano, $C_1$–$C_6$-alkyl, $C_1$–$C_3$haloalkyl, $C_1$–$C_6$alkoxy, $C_1$–$C_3$haloalkoxy, $C_1$–$C_3$alkylthio($C_1$–$C_3$alkoxy), $C_1$–$C_3$alkylthio, $C_1$–$C_3$alkoxy which is substituted by N—($C_1$–$C_2$alkyl)$_2$, or is $C_3$–$C_4$alkenyloxy, $C_3$–$C_4$alkenylthio, $C_1$–$C_3$alkylsulfonyl, $C_1$–$C_3$alkylsulfoxyl, $N(C_1$–$C_3$alkyl)$_2$, or a phenyl or benzyl group which are both unsubstituted or substituted by one to three identical or different members selected from fluorine, chlorine, bromine, nitro, cyano, methoxy, $C_1$–$C_4$alkyl, dimethylamino or $CF_3$; and $R_6$ and $R_7$ independently of the other are hydrogen, halogen, cyano, thiocyano, $C_1$–$C_6$alkyl, $C_1$–$C_3$haloalkyl, $C_1$–$C_6$alkoxy, $C_1$–$C_3$alkoxy which is substituted by halogen, nitro, $C_1$–$C_3$alkoxy, $C_1$–$C_3$alkylthio or $N(C_1$–$C_4$alkyl)$_2$, or are $C_1$–$C_4$alkylthio, $C_1$–$C_3$alkylsulfonyl, $C_1$–$C_3$alkylsulfoxyl, $C_3$–$C_4$alkenyloxy, $C_3$–$C_4$-alkynylthio, $C_3$–$C_4$alkynyloxy, $C_3$–$C_4$alkynylthio or $N(C_1$–$C_3$alkyl)$_2$.

6. A compound of claim 5, wherein $R_4$ is hydrogen and the other substituents are as defined in claim 5.

7. A compound of claim 2, wherein $R_1$ is trifluoromethyl, $R_2$ is nitro, $R_3$ is hydrogen, $R_4$ is hydrogen or the —C(O)R' group, in which R' is $C_1$–$C_4$alkyl which is unsubstituted or substituted by halogen, $C_1$–$C_3$alkoxy or $C_1$–$C_3$alkylthio; $R_5$ is hydrogen, halogen, cyano, thiocyano, $C_1$–$C_6$alkyl, $C_1$–$C_3$haloalkyl, $C_1$–$C_6$alkoxy, $C_1$–$C_3$haloalkoxy, $C_1$–$C_3$alkylthio-($C_1$–$C_3$alkoxy), $C_1$–$C_3$alkylthio, $C_1$–$C_3$alkoxy which is substituted by N—($C_1$–$C_2$alkyl)$_2$, or is $C_3$–$C_4$alkenyloxy, $C_3$–$C_4$alkenylthio, $C_1$–$C_3$alkylsulfonyl, $C_1$–$C_3$alkylsulfoxyl, N($C_1$–$C_3$alkyl)$_2$, or a phenyl or benzyl group which are both unsubstituted or substituted by one to three identical or different members selected from fluorine, chlorine, bromine, nitro, cyano, methoxy, $C_1$–$C_4$alkyl, dimethylamino or $CF_3$; and $R_6$ and $R_7$ independently of the other are hydrogen, halogen, cyano, thiocyano, $C_1$–$C_6$alkyl, $C_1$–$C_3$haloalkyl, $C_1$–$C_6$alkoxy, $C_1$–$C_3$alkoxy which is substituted by $C_1$–$C_3$alkylthio or N($C_1$–$C_4$alkyl)$_2$, or are $C_1$–$C_4$alkylthio, $C_1$–$C_3$alkylsulfonyl, $C_1$–$C_3$alkylsufoxyl, $C_3$–$C_4$alkenyloxy, $C_3$–$C_4$alkenylthio, $C_3$–$C_4$alkynyloxy, $C_3$–$C_4$alkynylthio or N($C_1$–$C_3$alkyl)$_2$.

8. A compound of claim 7, wherein $R_4$ is hydrogen and the other substituents are as defined in claim 7.

9. A compound of claim 1, selected from the group consisting of:

N-(3'-chloro-2',6'-dinitro-4'-trifluoromethylphenyl)-5-amino-4-chloro-6-methoxypyrimidine (compound 1.1), N-(3'-chloro-2',6'-dinitro-4'-trifluoromethylphenyl)-5-amino-4,6-dimethylthiopyrimidine (compound 1.2), N-(3'-chloro-2',6'-dinitro-4'-trifluoromethylphenyl)-5-amino-4,6-ditrifluoroethoxypyrimidine (compound 1.3), N-(3'-chloro-2',6'-dinitro-4'-trifluoromethylphenyl)-5-amino-4,6-dichloropyrimidine (compound 1.4), N-(3'-chloro-2',6'-dinitro-4'-trifluoromethylphenyl)-5-amino-4-chloro-6-methylmercaptopyrimidine (compound 1.184), N-(3'-chloro-2',6'-dinitro-4'-trifluoromethylphenyl)-5-amino-4-chloro-2-methyl-6-methoxypyrimidine (compound 1.205), N-(3-chloro-2',6'-dinitro-4'-trifluoromethylphenyl)-5-amino-2-chloro-4-methoxypyrimidine (compound 1.51), N-(3'-chloro-2',6'-dinitro-4'-trifluoromethylphenyl)-5-amino-2,4-dichloropyrimidine (compound 1.49), N-(3'-chloro-2',6'-dinitro-4'-trifluoromethylphenyl)-5-amino-2-chloro-4-allyloxypyrimidine (compound 1.210), N-(3'-chloro-2',6'-dinitro-4'-trifluoromethylphenyl)-5-amino-2-chloro-4-allylmercaptopyrimidine (compound 1.57), N-(3'-chloro-2',6'-dinitro-4'-trifluoromethylphenyl)-5-amino-2-chloro-4-propargyloxypyrimidine (compound 1.211), N-(3'-chloro-2',6'-dinitro-4'-trifluoromethylphenyl)-5-amino-4,6-dichloro-2-methylpyrimidine (compound 1.96), N-(3'-chloro-2',6'-dinitro-4'-trifluoromethylphenyl)-5-amino-4,6-dichloro-2-phenylpyrimidine (compound 1.125), N-(2',6'-dinitro-4'-trifluoromethylphenyl)-5-amino-4,6-dichloropyrimidine (compound 2.4), N-(2',4-dinitro-6'-trifluoromethylphenyl)-5-amino-4,6-dichloropyrimidine (compound 3.4), N-(2',4',6'-trinitrophenyl)-5-amino-4,6-dichloropyrimidine (compound 7.1), N-(2'-nitro-4'-trifluoromethylphenyl)-5-amino-4,6-dichloropyrimidine (compound 8.1).

10. A composition for controlling or preventing attack by phytopathogenic pests against plants, which contains at least one compound of claim 1, in an amount sufficient to control said pests, together with conventional adjuvants and carriers.

11. A method of controlling phytopathogenic pests or of preventing cultivated plants from being attacked by such pests, which comprises applying to said plants or to the locus thereof an effective amount of a compound of claim 1.

* * * * *